United States Patent
Kainth et al.

(10) Patent No.: US 7,297,395 B2
(45) Date of Patent: Nov. 20, 2007

(54) SUPERABSORBENT MATERIALS HAVING LOW, CONTROLLED GEL-BED FRICTION ANGLES AND COMPOSITES MADE FROM THE SAME

(75) Inventors: Arvinder Pal Singh Kainth, Neenah, WI (US); Richard Norris Dodge, II, Appleton, WI (US); Joseph Raymond Feldkamp, Appleton, WI (US); Stacy Averic Mundschau, Oshkosh, WI (US); Estelle Anne Ostgard, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 211 days.

(21) Appl. No.: 10/461,052

(22) Filed: Jun. 13, 2003

(65) Prior Publication Data

US 2004/0030312 A1   Feb. 12, 2004

Related U.S. Application Data

(60) Provisional application No. 60/399,877, filed on Jul. 30, 2002.

(51) Int. Cl.
*B32B 7/08*  (2006.01)
*B32B 27/04* (2006.01)

(52) U.S. Cl. .................. 428/292.1; 442/97; 442/99; 442/100; 442/118; 442/414; 442/417

(58) Field of Classification Search ............... 428/281, 428/283, 292.1; 604/368; 442/97, 99, 100, 442/118, 414, 417
See application file for complete search history.

(56) References Cited

U.S. PATENT DOCUMENTS 3,308,826 A    3/1967  Blake
3,338,992 A    8/1967  Kinney
3,341,394 A    9/1967  Kinney
3,502,538 A    3/1970  Petersen (Continued)

FOREIGN PATENT DOCUMENTS

EP    0 049 944 B1    11/1984

(Continued)

OTHER PUBLICATIONS

American Society for Testing Materials (ASTM) Designation: D 1921-89, "Standard Test Methods for Particle Size (Sieve Analysis) of Plastic Materials," pp. 493-496, published Aug. 1989.

(Continued)

*Primary Examiner*—Rena Dye
*Assistant Examiner*—Camie S. Thompson
(74) *Attorney, Agent, or Firm*—Bryan R. Rosiejka

(57) ABSTRACT

The present invention relates to water swellable, water insoluble superabsorbent materials having controlled variable gel-bed friction angles. Controlling the gel-bed friction angle of the superabsorbent materials may allow control of the swelling of the material, the absorbency of the material, and/or the absorbency, resiliency, and porosity of the absorbent composite containing the superabsorbent material. The present invention relates to treatments for superabsorbent materials to manipulate friction angle and new superabsorbent materials having the desired friction angle characteristics. The present invention also relates to absorbent composites employing superabsorbent materials having the desired friction angle characteristics.

52 Claims, 8 Drawing Sheets

U.S. PATENT DOCUMENTS

| | | | |
|---|---|---|---|
| 3,502,763 A | 3/1970 | Hartmann | |
| 3,542,615 A | 11/1970 | Dobo et al. | |
| 3,692,618 A | 9/1972 | Dorschner et al. | |
| 3,795,538 A | 3/1974 | Evans et al. | |
| 3,802,817 A | 4/1974 | Matsuki et al. | |
| 3,849,241 A | 11/1974 | Butin et al. | |
| 3,943,079 A | 3/1976 | Hamed | 524/14 |
| 4,064,057 A | 12/1977 | Koerner et al. | 252/8.84 |
| 4,340,563 A | 7/1982 | Appel et al. | |
| 4,341,215 A | 7/1982 | Eldridge | |
| 4,432,759 A * | 2/1984 | Gross et al. | 604/411 |
| 4,548,847 A | 10/1985 | Aberson et al. | |
| 4,637,957 A | 1/1987 | Murase | 428/395 |
| 4,663,220 A | 5/1987 | Wisneski et al. | 428/221 |
| 4,724,114 A | 2/1988 | McFarland et al. | 264/510 |
| 4,880,858 A | 11/1989 | Farrar et al. | |
| 4,940,464 A | 7/1990 | Van Gompel et al. | 604/396 |
| 4,980,231 A | 12/1990 | Baker et al. | |
| 5,046,272 A | 9/1991 | Vogt et al. | 38/143 |
| 5,064,653 A | 11/1991 | Sessions et al. | 424/445 |
| 5,082,723 A | 1/1992 | Gross et al. | |
| 5,104,116 A | 4/1992 | Pohjola | 271/188 |
| 5,147,343 A * | 9/1992 | Kellenberger | 604/368 |
| 5,175,046 A | 12/1992 | Nguyen | |
| 5,188,624 A | 2/1993 | Young et al. | |
| 5,224,405 A | 7/1993 | Pohjola | 83/24 |
| 5,226,992 A | 7/1993 | Morman | 156/62.4 |
| 5,244,735 A | 9/1993 | Kimura et al. | |
| 5,308,896 A | 5/1994 | Hansen et al. | 524/13 |
| 5,338,766 A | 8/1994 | Phan et al. | |
| 5,352,480 A | 10/1994 | Hansen et al. | 427/202 |
| 5,496,933 A | 3/1996 | Kelkenberg | |
| 5,538,783 A | 7/1996 | Hansen et al. | 442/417 |
| 5,547,541 A | 8/1996 | Hansen et al. | 462/12 |
| 5,547,745 A | 8/1996 | Hansen et al. | 442/417 |
| 5,562,646 A | 10/1996 | Goldman et al. | 604/368 |
| 5,571,618 A | 11/1996 | Hansen et al. | |
| 5,589,256 A | 12/1996 | Hansen et al. | 442/417 |
| 5,601,542 A | 2/1997 | Melius et al. | |
| 5,607,759 A | 3/1997 | Hansen et al. | 442/417 |
| 5,607,760 A | 3/1997 | Roe | 442/338 |
| 5,609,587 A | 3/1997 | Roe | |
| 5,620,565 A | 4/1997 | Lazorisak et al. | 162/72 |
| 5,641,561 A | 6/1997 | Hansen et al. | 442/417 |
| 5,672,418 A | 9/1997 | Hansen et al. | 442/70 |
| 5,693,411 A | 12/1997 | Hansen et al. | |
| 5,800,419 A | 9/1998 | Soga et al. | |
| 5,803,920 A | 9/1998 | Gilman | 604/378 |
| 5,830,317 A | 11/1998 | Vinson et al. | 162/125 |
| 5,833,678 A | 11/1998 | Ashton et al. | 428/364 |
| 5,855,571 A | 1/1999 | Steger et al. | |
| 5,906,890 A | 5/1999 | Taniguchi et al. | 428/364 |
| 5,941,862 A | 8/1999 | Haynes et al. | |
| 5,985,432 A | 11/1999 | Wang et al. | |
| 6,022,818 A | 2/2000 | Welchel et al. | |
| 6,033,769 A | 3/2000 | Brueggemann et al. | 428/305.5 |
| 6,068,924 A | 5/2000 | Palumbo | |
| 6,153,209 A | 11/2000 | Vega et al. | 424/101 |
| 6,176,849 B1 | 1/2001 | Yang et al. | |
| 6,190,678 B1 | 2/2001 | Hasenoehrl et al. | 162/164.1 |
| 6,217,889 B1 | 4/2001 | Lorenzi et al. | 424/401 |
| 6,231,605 B1 | 5/2001 | Ku | |
| 6,231,721 B1 | 5/2001 | Quick et al. | 162/164.1 |
| 6,258,996 B1 | 7/2001 | Goldman | |
| 6,340,411 B1 | 1/2002 | Hansen et al. | 162/173 |
| 6,380,456 B1 | 4/2002 | Goldman | |
| 6,391,953 B1 | 5/2002 | Hütte et al. | |
| 6,395,830 B1 | 5/2002 | Jonas et al. | |
| 6,433,058 B1 | 8/2002 | Weir et al. | |
| 6,455,114 B1 | 9/2002 | Goldhirsch et al. | |
| 2001/0049514 A1 | 12/2001 | Dodge, II et al. | |
| 2002/0045869 A1 | 4/2002 | Dodge, II et al. | |
| 2002/0155281 A1 | 10/2002 | Lang et al. | 428/321 |
| 2002/0158397 A1 | 10/2002 | Wilfer et al. | 270/52.01 |
| 2004/0023579 A1 | 2/2004 | Kainth et al. | |
| 2004/0023589 A1 | 2/2004 | Kainth et al. | |

FOREIGN PATENT DOCUMENTS

| | | |
|---|---|---|
| EP | 0 157 960 A1 | 10/1985 |
| EP | 0 197 355 A2 | 10/1986 |
| EP | 0 217 032 B1 | 2/1992 |
| EP | 0 526 225 A1 | 2/1993 |
| EP | 0 576 738 A1 | 1/1994 |
| EP | 0 618 329 A1 | 10/1994 |
| EP | 0 648 800 A2 | 4/1995 |
| EP | 0 666 350 A1 | 8/1995 |
| EP | 0 875 233 A1 | 11/1998 |
| EP | 0 809 722 B1 | 2/2000 |
| EP | 0 774 943 B1 | 5/2000 |
| EP | 1 145 724 A1 | 10/2001 |
| EP | 1 253 560 A1 | 10/2002 |
| EP | 1 264 605 A1 | 12/2002 |
| GB | 689640 A | 4/1953 |
| JP | 50-105911 A | 8/1975 |
| JP | 08-049166 A | 2/1996 |
| JP | 10-008380 A | 1/1998 |
| JP | 10-057727 A | 3/1998 |
| WO | WO 91/05106 A1 | 4/1991 |
| WO | WO 95/22655 A1 | 8/1995 |
| WO | WO 95/34373 A1 | 12/1995 |
| WO | WO 96/17681 A1 | 6/1996 |
| WO | WO 96/24719 A2 | 8/1996 |
| WO | WO 97/12575 A1 | 4/1997 |
| WO | WO 97/21856 A1 | 6/1997 |
| WO | WO 97/49855 A1 | 12/1997 |
| WO | WO 98/52745 A1 | 11/1998 |
| WO | WO 98/55159 A2 | 12/1998 |
| WO | WO 99/32165 A1 | 7/1999 |
| WO | WO 99/49826 A1 | 10/1999 |
| WO | WO 00/62730 A1 | 10/2000 |
| WO | WO 00/62825 * | 10/2000 |
| WO | WO 00/62825 A2 | 10/2000 |
| WO | WO 00/63487 A1 | 10/2000 |
| WO | WO 01/13966 A1 | 3/2001 |
| WO | WO 01/22909 A1 | 4/2001 |
| WO | WO 01/66056 A1 | 9/2001 |
| WO | WO 01/87215 A1 | 11/2001 |
| WO | WO 01/91684 A2 | 12/2001 |
| WO | WO 02/49565 A2 | 6/2002 |
| WO | WO 02/056812 A2 | 7/2002 |
| WO | WO 02/70125 A1 | 9/2002 |
| WO | WO 02/072951 A2 | 9/2002 |
| WO | WO 03/057964 A1 | 7/2003 |
| WO | WO 2004/011042 A2 | 2/2004 |
| WO | WO 2004/020010 A1 | 3/2004 |

OTHER PUBLICATIONS

Holtz, Robert D. and William D. Kovacs, "The Mohr Circle, Failure Theories, Stress Paths," *An Introduction to Geotechnical Engineering*, Prentice-Hall, Inc., New Jersey, 1981, Chapter 10, pp. 431-484.

Bronkhorst, Curt A. and Keith A. Bennett, "Deformation and Failure Behavior of Paper," Chapter 7, *Handbook of Physical Testing of Paper*, Second Edition, vol. 1, edited by Richard E. Mark et al., Marcel Dekker, Inc., New York, 2002, pp. 313, 345-349.

Fellers, Christer and Benjamin C. Donner, "Edgewise Compression Strength of Paper," Chapter 9, *Handbook of Physical Testing of Paper*, Second Edition, vol. 1, edited by Richard E. Mark et al., Marcel Dekker, Inc., New York, 2002, pp. 481, 499-503.

* cited by examiner

SUPERABSORBENT MATERIALS HAVING LOW, CONTROLLED GEL-BED FRICTION ANGLES AND COMPOSITES MADE FROM THE SAME

This application claims priority from U.S. Provisional Application No. 60/399,877 filed on Jul. 30, 2002.

BACKGROUND

People rely on absorbent articles in their daily lives.

Absorbent articles, including adult incontinence articles, feminine care articles, and diapers, are generally manufactured by combining a substantially liquid-permeable topsheet; a substantially liquid-impermeable backsheet attached to the topsheet; and an absorbent core located between the topsheet and the backsheet. When the article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core is designed to have desirable physical properties, e.g. a high absorbent capacity and high absorption rate, so that bodily fluids may be transported from the skin of the wearer into the disposable absorbent article.

The present invention relates to water swellable, water insoluble superabsorbent materials, which are often employed in an absorbent core (also referred to as an absorbent composite), in part to help "lock up" fluids entering the core. More specifically, the present invention pertains to superabsorbent materials having a modified friction angle measured in a gel-bed of the superabsorbent material. The gel-bed friction angle of the superabsorbent materials of the present invention is controllable and follows a predetermined pattern. The present invention also relates to use of the controlled gel-bed friction angle superabsorbent materials in absorbent composites and absorbent articles incorporating such absorbent composites. Controlling the gel-bed friction angle of the superabsorbent materials may allow control of phenomena including, but not limited to: the swelling of the superabsorbent material, stresses experienced by the superabsorbent material and/or other ingredients (e.g., fibers) in an absorbent composite; the permeability of an absorbent composite containing the superabsorbent material; and/or, the absorbency, resiliency, and porosity of the absorbent composite. The present invention relates to treatments for superabsorbent materials to manipulate gel-bed friction angle and new superabsorbent materials having the desired gel-bed friction angle characteristics.

Absorbent composites used in absorbent articles typically consist of an absorbent material, such as a superabsorbent material, mixed with a composite matrix containing natural and/or synthetic fibers. As fluids enter the absorbent composite, the superabsorbent material swells as it absorbs the fluids. The superabsorbent material contacts the surrounding matrix components and possibly other superabsorbent material as it swells. The full swelling capacity of the superabsorbent material may be reduced due to stresses acting on the superabsorbent materials (e.g., stresses imposed by the matrix on superabsorbent material; external stresses acting on the absorbent composite that comprises a matrix and superabsorbent material, including, for example, stresses imposed on an absorbent composite by a wearer during use; stresses imposed by one portion of the superabsorbent material on another portion of the superabsorbent material, whether directly or indirectly; etc.). Furthermore, stresses acting on an absorbent composite comprising the superabsorbent material may act to reduce interstitial pore volume, i.e., space between superabsorbent material, fibers, other ingredients, or some combination thereof (without being bound to a particular analogy, and for purposes of explanation only, think of a force acting on some unit area of a sponge-like material with pores, with the force per unit area—i.e., stress—acting to reduce the thickness of the sponge-like material, and, therefore, the volume of the pores).

As the superabsorbent material swells, it may rearrange into void spaces of the absorbent composite matrix as well as expand readily against the matrix to create additional void space. Also, as the superabsorbent material swells, stresses acting within and/or on the absorbent composite may increase due—at least in part—to expansion of the superabsorbent material, thereby reducing the pore volume between: fibers, superabsorbent material, other ingredients in the absorbent composite, or some combination there of. The ability to rearrange within the composite matrix, and the magnitude and extent of the stresses acting within and on the composite matrix, depend on several factors specifically including a gel-bed friction angle of the superabsorbent material. In addition, as the superabsorbent material moves within the composite matrix, the superabsorbent material may contact the components, such as fibers and binding materials, of the surrounding matrix. Thus, the frictional properties of the superabsorbent material may influence the ability of the material to swell and rearrange or move within the matrix, as well as the magnitude and extent of the stresses acting within and on the composite matrix.

It is often desired that the superabsorbent material be able to rotate and translate within the voids of the absorbent composite to allow the superabsorbent material to swell as close to full swelling capacity as is possible within the matrix. There is a need for a superabsorbent material which may more easily rearrange within the void space of the absorbent composite matrix. There is a need for a way to control the physical mechanics that: allow the superabsorbent material to rearrange within the absorbent composite matrix; reduce or minimize the stresses acting within or on the absorbent composite or its ingredient(s); and/or reduce the reduction in pore volume that may accompany the build up of said stresses.

SUMMARY

We have discovered that superabsorbent materials having controlled gel-bed friction angles meet one or more of these needs. Accordingly, the present invention is directed to superabsorbent materials having controlled gel-bed friction angles. The superabsorbent materials of the present invention have gel-bed friction angles that follow controlled gel-bed friction angle patterns substantially different than gel-bed friction angle patterns followed by conventional superabsorbent materials. The superabsorbent materials of the present invention may be produced using non-conventional manufacturing processes to obtain desired gel-bed friction angles or by treating with friction angle increasing additives and/or friction angle reducing additives to increase, decrease, or otherwise control the friction angle of the superabsorbent gel-bed during swelling. Gel-bed friction angle is a property of a gel-bed or superabsorbent material coming from Mohr-Coulomb failure theory. A lower friction angle implies lower inter-particle friction.

The superabsorbent material of the present invention may be a water swellable, water insoluble superabsorbent material. The water swellable, water insoluble superabsorbent material may have a first gel-bed friction angle at a superabsorbent material swelling level of about 2.0 grams of 0.9 weight percent sodium chloride solution/gram of the superabsorbent material and gel-bed friction angles, at superabsorbent material swelling levels greater than about 2.0 grams of 0.9 weight percent sodium chloride solution/gram of the superabsorbent material, substantially equal to or less than the first gel-bed friction angle. The first gel-bed friction angle may be about 20 degrees or less. In other embodiments, the gel-bed friction angles may be greater than the first gel-bed friction angle. The superabsorbent material of the present invention may be utilized in an absorbent composite further comprising a plurality of wettable fibers.

These and other features, aspects, and advantages of the present invention will become better understood with regard to the following description, appended claims, and accompanying drawings.

BRIEF DESCRIPTION OF DRAWINGS OF EXAMPLES AND/OR REPRESENTATIVE EMBODIMENTS

DEFINITIONS

Figure 1:
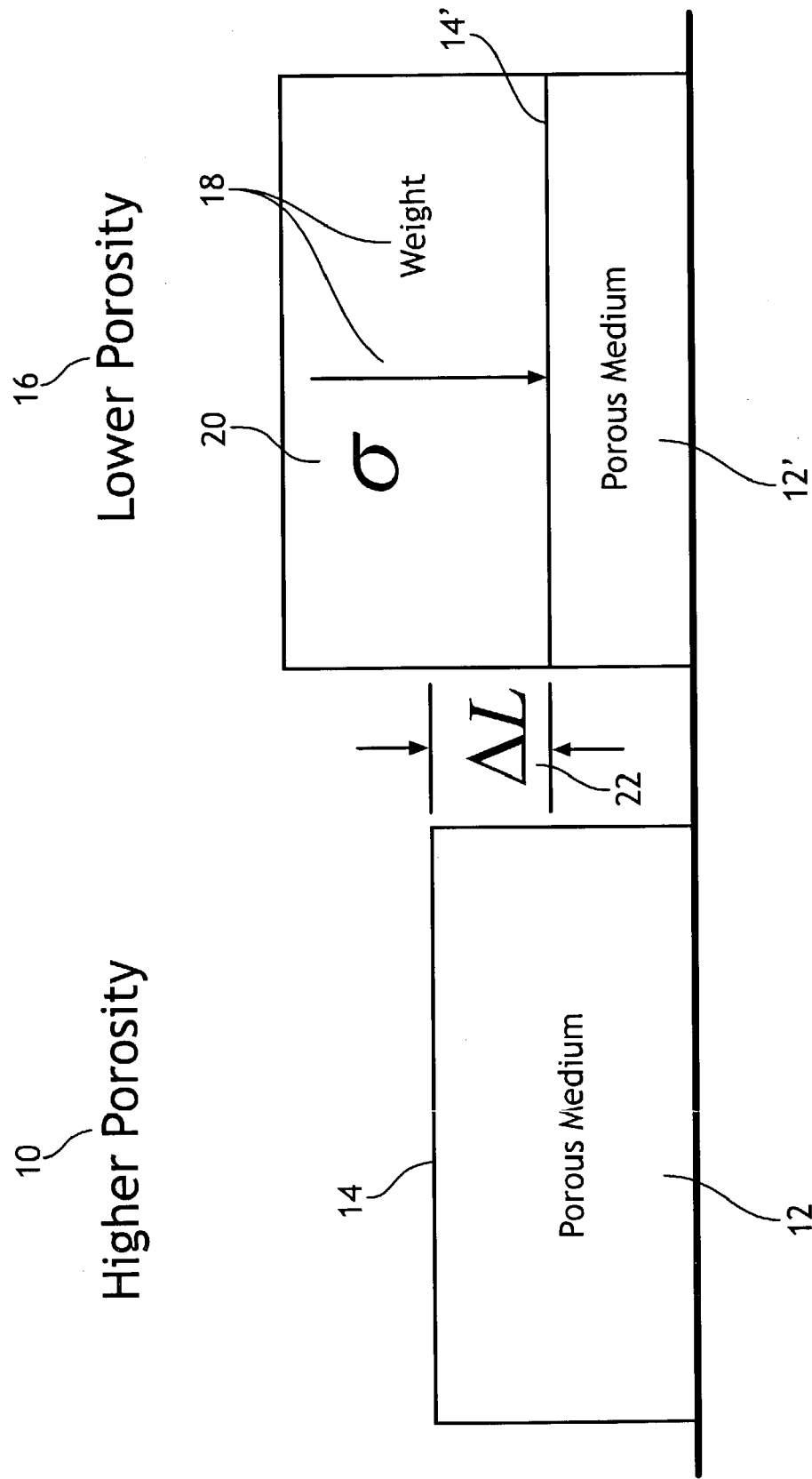
FIG. 1 shows an example of a response of a porous medium to a stress (i.e., a force per unit area) acting on the medium.

Within the context of this specification, each term or phrase below will include the following meaning or meanings.

"Absorbency Under Load" (AUL) refers to the measure of the liquid retention capacity of a material under mechanical load. It is determined by a test which measures the amount, in grams, of a 0.9% by weight aqueous sodium chloride solution a gram of material may absorb in 1 hour under an applied load or restraining pressure of about 0.3 pound per square inch (2,000 Pascals). A procedure for determining AUL is provided in U.S. Pat. No. 5,601,542, which is incorporated by reference in its entirety in a manner consistent herewith.

"Absorbent article" includes, without limitation, diapers, training pants, swim wear, absorbent underpants, baby wipes, incontinence products, feminine hygiene products and medical absorbent products (for example, absorbent medical garments, underpads, bandages, drapes, and medical wipes).

"Fiber" and "Fibrous Matrix" includes, but is not limited to natural fibers, synthetic fibers and combinations thereof. Examples of natural fibers include cellulosic fibers (e.g., wood pulp fibers), cotton fibers, wool fibers, silk fibers and the like, as well as combinations thereof. Synthetic fibers can include rayon fibers, glass fibers, polyolefin fibers, polyester fibers, polyamide fibers, polypropylene. As used herein, it is understood that the term "fibrous matrix" includes a plurality of fibers. "Free Swell Capacity" refers to the result of a test which measures the amount in grams of an aqueous 0.9% by weight sodium chloride solution that a gram of material may absorb in 1 hour under negligible applied load.

"Gel-bed friction angle" refers to the friction angle of a superabsorbent material in a gel-bed as measured with a Jenike-Shulze ring shear tester or other friction angle measuring technique.

"Gradient" refers to a graded change in the magnitude of a physical quantity, such as the quantity of superabsorbent material present in various locations of an absorbent pad, or other pad characteristics such as mass, density, or the like.

"Gel-bed" refers to an amount of superabsorbent material within a container such as a ring shear cell.

"Homogeneously mixed" refers to the uniform mixing of two or more substances within a composition, such that the magnitude of a physical quantity of each of the substances remains substantially consistent throughout the composition.

"Incontinence products" includes, without limitation, absorbent underwear for children, absorbent garments for children or young adults with special needs such as autistic children or others with bladder/bowel control problems as a result of physical disabilities, as well as absorbent garments for incontinent older adults.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are suitably substantially continuous in length. "Mohr circle" refers to a graphical representation of the state of stress within a material subjected to one or more forces. Mohr circles are described in more detail below.

"Mohr failure envelope" refers to the failure shear stress at the failure plane as a function of the normal stress on that failure or shear plane. Mohr failure envelopes are described in more detail below.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Superabsorbent" or "superabsorbent material" refers to a water-swellable, water-insoluble organic or inorganic material capable, under the most favorable conditions, of absorbing at least about 10 times its weight and, more particularly, at least about 20 times its weight in an aqueous solution containing 0.9 weight percent sodium chloride. The superabsorbent materials may be natural, synthetic and modified natural polymers and materials. In addition, the superabsorbent materials may be inorganic materials, such as silica gels, or organic compounds such as cross-linked polymers. The superabsorbent materials of the present invention may embody various structure configurations including particles, fibers, flakes, and spheres.

"Pattern" or "predetermined pattern" when mentioned in context with gel-bed friction angle refers to a particular dependence of the gel-bed friction angle on the swelling level of the superabsorbent material. The pattern of the gel-bed friction angle may refer to the changes in the gel-bed friction angle of a superabsorbent material as a function of the swelling level of the superabsorbent material.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al.; U.S. Pat. No. 3,692,618 to Dorschner et al.; U.S. Pat. No. 3,802,817 to Matsuki et al.; U.S. Pat. Nos. 3,338,992 and 3,341,394 to Kinney; U.S. Pat. No. 3,502,763 to Hartmann; U.S. Pat. No. 3,502,538 to Petersen; and, U.S. Pat. No. 3,542,615 to Dobo et al., each of which is incorporated by reference in its entirety in a manner consistent herewith. Spunbond fibers are quenched and generally not tacky when they are deposited onto a collecting surface. Spunbond fibers are generally continuous and often have average deniers larger than about 0.3, more particularly, between about 0.6 and 10.

These terms may be defined with additional language in the remaining portions of the specification.

Overview of Continuum Mechanics, Mohr Circles, and Mohr-Coulomb Failure Theory

Given that our discovery is described using tools and terminology from mechanics, an overview of continuum mechanics, Mohr circles, and Mohr-Coulomb failure theory is provided for convenience. It should be understood that this overview is for purposes of explanation only—it provides an analytic framework for characterizing the present invention, and should not be viewed as limiting the present invention disclosed herein.

Absorbent articles and composites are porous by nature. The open space between the various ingredients that make up the composite (e.g., superabsorbent material and fibers) is commonly referred to as void space or pore space. Pore space acts to store liquids and/or provide a conduit or pathway for transporting liquid throughout the absorbent composite or article. The volume of pore space per unit volume of absorbent composite is commonly referred to as "porosity." Generally absorbency performance is improved by increasing porosity. For example, permeability of an absorbent composite—i.e., the ability of the composite to facilitate liquid transport—increases with increasing porosity (other factors, such as specific surface area and tortuosity, being equal).

The application of a stress to a porous medium, such as an absorbent composite or article, is known to cause a volumetric deformation of the medium as a whole, as well as shear deformation in the case of anisotropic stresses. FIG. 1 depicts an example of a volumetric deformation of a porous medium. The left-most image of FIG. 1 is labeled "Higher Porosity" 10 and shows a porous medium 12 without a weight applied to the uppermost planar surface 14 of the porous medium 12 (with the uppermost planar area having some discrete area): The right-most image of FIG. 1 is labeled "Lower Porosity" 16 and shows the same porous medium 12' with a weight 18 applied to the uppermost planar surface 14' of the porous medium 12'. In response to the placement of the weight 18, which produces a stress, or normal force per unit area, σ 20, the thickness decreases (as denoted by Δ L 22). (Note: for purposes of the present invention, compressive stresses are represented as having positive values.)

For a porous medium 12 made up of individual ingredients such as superabsorbent particles and fibers (e.g., an absorbent composite), the thickness change of the porous medium 12 as a whole, Δ L 22, likely does not result from a reduction in the individual dimensions of individual particles and fibers (reductions in these individual thicknesses would likely be small or negligible). Instead, the decrease in the thickness of the porous medium 12 as a whole, Δ L 22, results from a reduction in porosity (or, analogously, void volume). Accordingly, in the example depicted in FIG. 1, an increase in stress, or normal force per unit area, σ 22, reduces the thickness Δ L 22 of the porous medium 12 as a whole, and reduces the porosi fluid in the pores is a compressible gas, then a normal stress acting on the surface of the porous medium 12 would: compress the gas within the pores; or cause a portion of the gas within the pores to exit the porous medium 12; or, some combination thereof. If, in this same FIG. 1, a fluid in the pores is an incompressible liquid, then a normal stress acting on the surface of the porous medium 12 would cause a portion of the liquid to exit the porous medium 12.)

Figure 2:
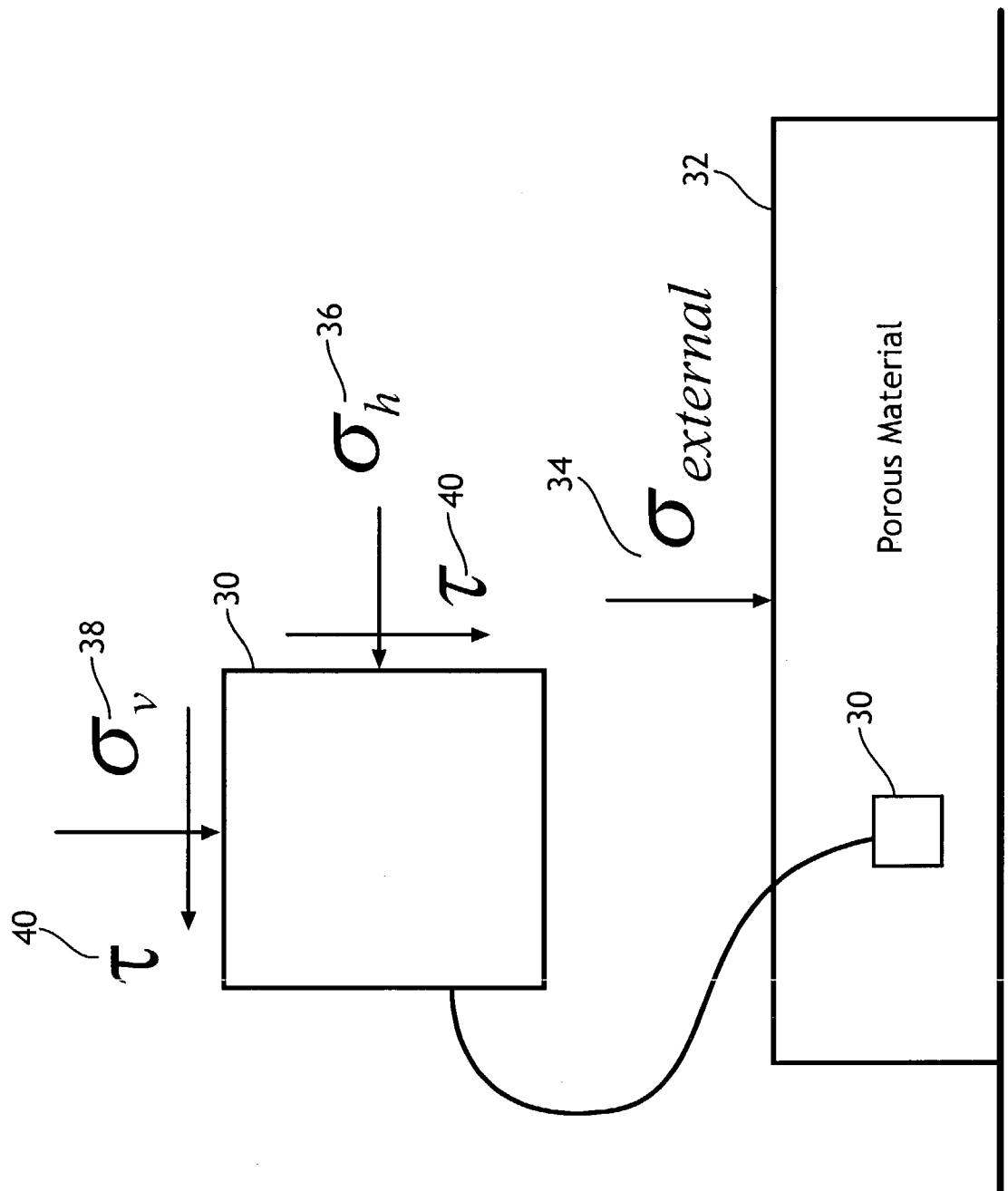
FIG. 2 shows an example of the state of stress of an arbitrary element at equilibrium in a porous medium.

The porous medium 12 of FIG. 1 may be examined further to analyze the stresses acting on an arbitrary element within the porous medium 12. FIG. 2 illustrates the state of stress of an arbitrary element 30—here represented by the face of a cube—at equilibrium (the arbitrary element is within a porous medium 32 being subjected to an external stress $\sigma_{external}$ 34). For present purposes, the arbitrary element 30 within the porous medium 32 is treated as a continuum. In FIG. 2, the state of stress is represented by two normal components of stress, $\sigma_h$ 36 acting horizontally on a face of the cube and σ, 38 acting vertically on another face of the cube, as well as a shear stress τ 40. The normal components of stress 36 are perpendicular to the faces of the arbitrary element 30, whereas the shear stresses 40 are parallel to the faces of the arbitrary element 10.

It should be noted that if the shear stresses 40 are zero (i.e., τ=0), then the two normal stresses 36 are referred to as principal stresses. Furthermore, when τ=0, then the larger of the two normal stresses 36 is called the major principal stress while the other is called the minor principal stress. For the present discussion, the two stresses are assumed to be principal stresses, with $\sigma_h \geq \sigma_v$.

There are generally at least two contributions to stress generation that combine to produce principal stresses such as those identified in FIG. 2. The first is an external stress 34, possibly non-uniform, acting on the boundary of the porous medium 32. This stress is transmitted throughout the porous medium 32 in accordance with well known force-balance equations. The second contribution arises due to swelling of components that make up the porous medium 32 (e.g., a superabsorbent material). For example, the swelling of blocks, or elements, immediately adjacent to the arbitrary element 30 depicted in FIG. 2, will cause an "internally"

generated stress acting on or along the arbitrary element 30 as other elements attempt to expand against it and each other.

Figure 3:
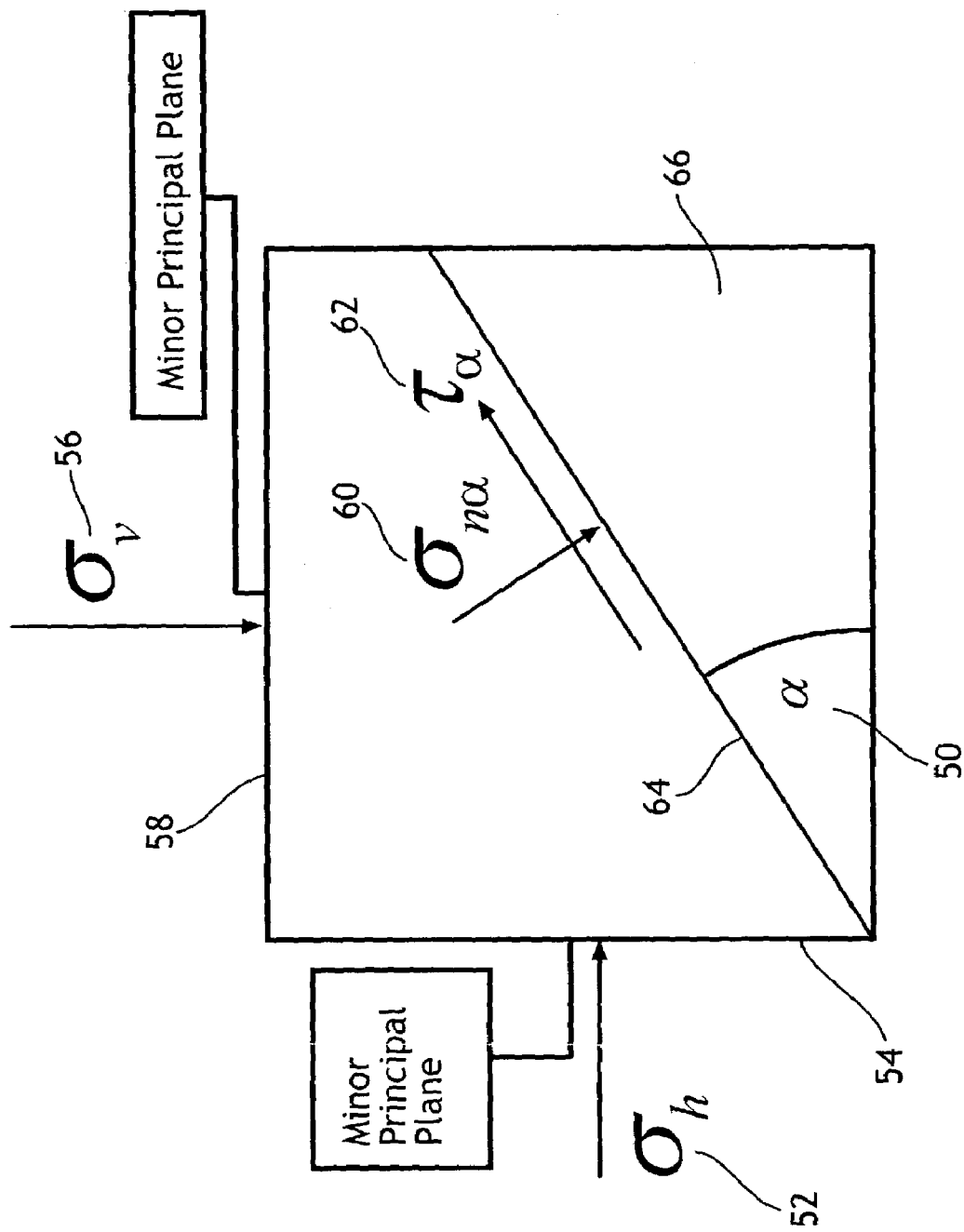
FIG. 3 shows an example of an arbitrary element and the normal forces and shear forces acting on a plane passing through the arbitrary element.

As stated above, when the stresses acting on an arbitrary element 30, such as that depicted in FIG. 2, are principal stresses, there are no shear stresses 40 acting on the faces of the arbitrary element 30. There is, however, shear stress 40 acting on other imaginary planes passing through the depicted arbitrary element 30—planes oriented at some angle α 50 away from horizontal, 0<α<90°, as shown in FIG. 3. FIG. 3 depicts a major principal stress $\sigma_h$ 52 acting on a major principal plane 54, and a minor principal stress $\sigma_v$ 56 acting on a minor principal plane 58. A normal stress $\sigma_{n\alpha}$ 60 and a shear stress $\tau_\alpha$ 62 act on the imaginary or arbitrary plane 64 oriented at angle α 50 away from horizontal.

Figure 4:
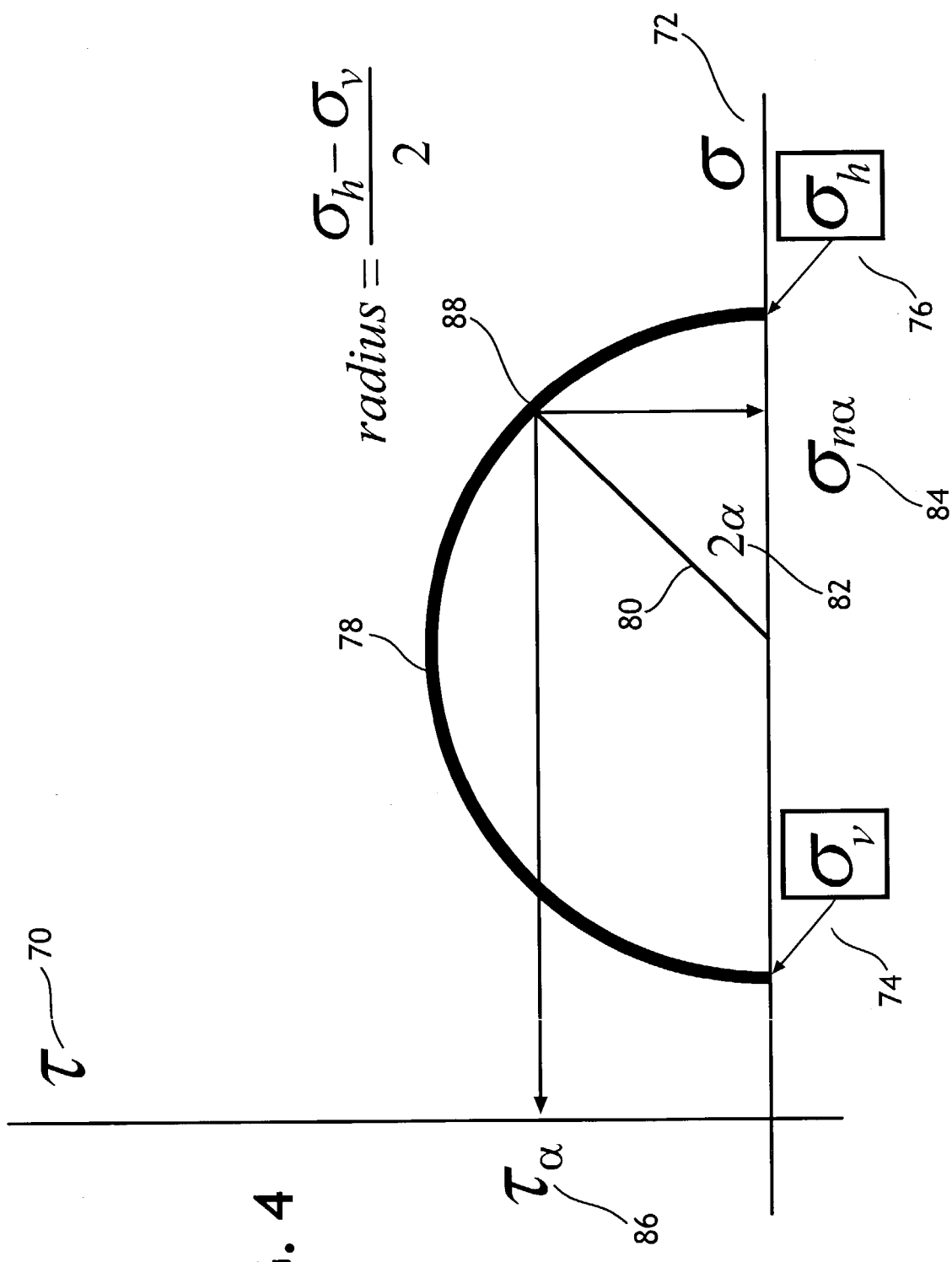
FIG. 4 shows an example of a Mohr Circle on a plot of shear stress (y axis) versus normal stress (x axis).

Obtaining the shear and normal forces 62 and 60, respectively, acting on the arbitrary plane 64 passing through the element 66 depicted in FIG. 3 is simplified by using the graphical approach of the Mohr circle, as illustrated in FIG. 4. FIG. 4 shows a plot of shear stress (y-axis) 70 as a function of normal stress (x-axis) 72. For purposes of the present discussion the principal stresses are assumed to be known (e.g., by calculation or measurement). The x-y coordinates of the minor principal stress $\sigma_v$ 74 and the major principal stress $\sigma_h$ 76 lie on the x-axis (i.e., where the shear stress τ 70 is equal to zero). A semi-circle 78 is drawn such that the coordinates of the minor and major principal stresses 74 and 76, respectively, correspond to the end points of the arc defining the perimeter of the semi-circle 78. The radius of this semi-circle 78 equals one-half of the difference between the major principal stress $\sigma_h$ 76 and the minor principal stress $\sigma_v$ 74. By constructing a radial line segment 80 at an angle 2α 82 from the x-axis, with one end of the radial line segment 80 corresponding to the center of the semi-circle 78, and other end corresponding to a point on the semi-circle arc closest to the major principal stress, both the normal stress, $\sigma_{n\alpha}$ 84, and the shear stress $\tau_\alpha$ 86 are obtained at the intersection 88 of the radial line segment 80 with the Mohr semi-circle 78.

Figure 5:
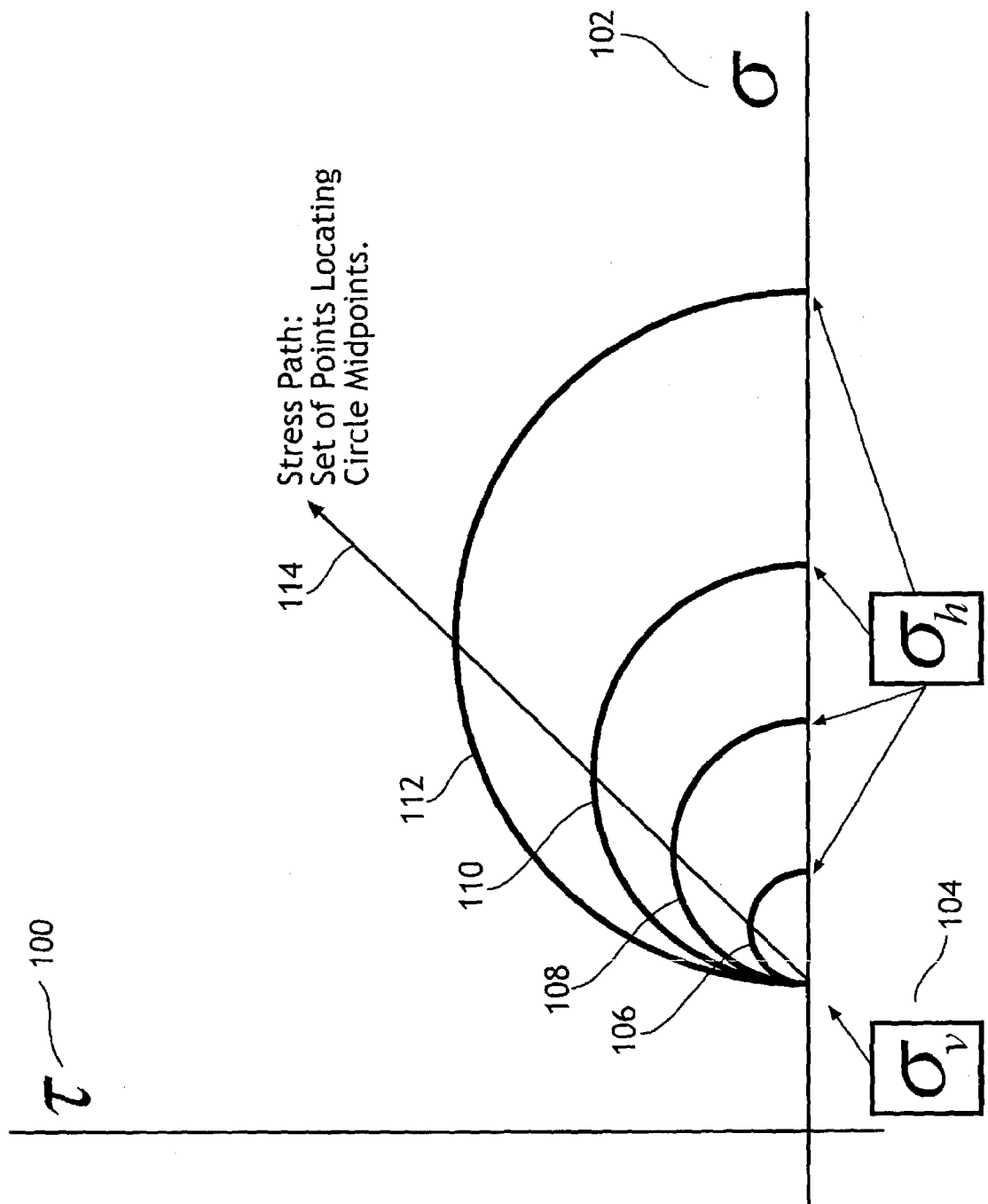
FIG. 5 shows an example of a sequence of Mohr Circles corresponding to one possible stress path on a plot of shear stress (y axis) versus normal stress (x axis).

FIG. 5 depicts one example of stress evolution for a porous medium that employs one or more swelling components (e.g., a particulate superabsorbent material). The y-axis again corresponds to shear stress τ 100, and the x-axis again corresponds to normal stress σ 102. If the minor principal stress $\tau_v$ 104 acting on an arbitary element from the porous medium remains unchanged, then stress development (which would accompany, for example, swelling of superabsorbent material) may be viewed as a family of Mohr circles 106, 108, 110, and 112, all of which have the same minor principal stress $\sigma_v$ 104. The progression of the Mohr circles 106, 108, 110, and 112 is commonly referred to as a stress path 114—more precisely, the line passing through the set of the Mohr circles 106, 108, 110, and 112 at points simultaneously locating the maximum shear stress and mean stress for each Mohr circle 106, 108, 110, and 112.

The center of each Mohr circle 106, 108, 110, and 112, which equates to the mean stress, determines the extent of the volumetric deformation of pore space contained within a particular arbitrary element, and may correspond to the approximate stress experienced by superabsorbent materials.

Stresses in a porous medium are not likely to increase indefinitely—rather, failure will take place, accompanied by sliding along particular failure planes (e.g., at the interface between superabsorbent material and fiber; or at the interface between individual particles of superabsorbent material; etc.). The Mohr-Coulomb failure criterion states that a shear force acting on a plane at failure will be linearly proportional to the normal force acting on that same plane, again at failure. Hence, Mohr-Coulomb theory provides a failure limit, or envelope, beyond which stable states of stress do not exist. If a line corresponding to this failure limit is superimposed on a plot of shear stress and normal stress depicting a Mohr circle 106, 108, 110, and 112 (which may be thought of as corresponding to a given state or degree of swelling for a porous medium employing a superabsorbent material), then the Mohr circle 106, 108, 110, and 112 may only increase in radius (e.g., by additional swelling of the porous medium and/or superabsorbent material employed by the porous medium) to the extent that it becomes tangent to this linear envelope.

Figure 6:
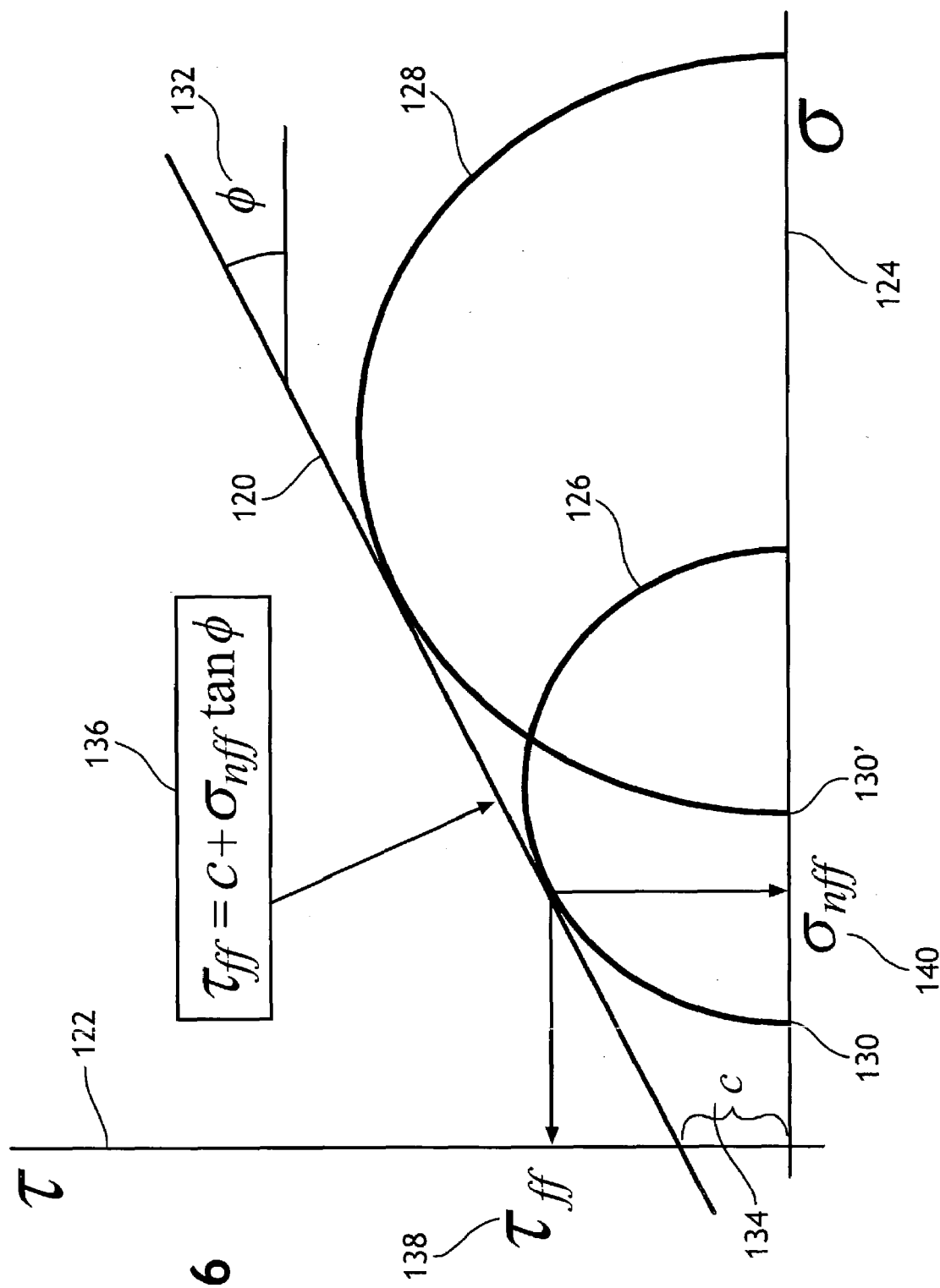
FIG. 6 shows an example of Mohr Circles in relation to a Mohr-Coulomb failure envelope on a plot of shear stress (y axis) versus normal stress (x axis).

FIG. 6 depicts a linear failure envelope 120 on a plot of shear stress τ 122 versus normal stress σ 124. On this plot are depicted each Mohr circle having a different value of initial stress—that is, two different values of the minor principal stress $\sigma_v$ 130 and 130'. The friction angle φ 132 and cohesion c 134 are properties of a particular material (e.g., an absorbent composite comprising fiber and superabsorbent material; a gel bed of swollen, particulate superabsorbent material; etc.). The tangent of the friction angle φ 132, which is equivalent to the coefficient of static friction from elementary physics, measures the extent to which an increasing normal force permits a larger maximum shear force. Cohesion c 134 represents the amount of shear stress a material will tolerate before failure in the absence of any normal force on the proposed failure plane. An increase in any one of the three parameters—friction angle φ 132, cohesion c 134, or minor principle stress $\sigma_v$ 130 and 130'—will permit the development of larger stresses in a porous material—i.e., a larger Mohr circle. Friction angle φ 132 and cohesion c 134 are properties of the material and may be measured (e.g., using the test and methodology disclosed herein). FIG. 6 also depicts the mathematical relationship $\tau_{ff} = c + \sigma_{nff} (\tan \phi)$ 136, which relates friction angle φ 132, cohesion c 134, shear stress at failure $\tau_{ff}$ 138, and normal stress at failure $\sigma_{nff}$ 140. (Note: for purposes of this disclosure, $\sigma_{nff}$ is equivalent to $\sigma_{ff}$, with both terms referring to a normal stress acting on the failure plane at failure.) This relationship is described in more detail below in the Detailed Description section.

As stated earlier, it is generally advantageous to minimize or decrease the reduction of porosity, or void volume, that results from the application of a compressive stress to an absorbent article. By choosing materials that limit stress increases (e.g., low, controlled gel-bed friction angle superabsorbent material) the magnitude of porosity reductions may be decreased. For example, low, controlled gel-bed friction angle superabsorbent material will promote the onset of failure before stresses rise to values that cause significant losses of porosity, and therefore permeability. An additional benefit of providing stress relief through low, controlled gel-bed friction angle materials is that such superabsorbent materials will retain a larger portion of their free-swell capacity—since it is well known that superabsorbent capacity decreases with increasing loading.

DETAILED DESCRIPTION OF REPRESENTATIVE EMBODIMENTS

The present invention relates to water swellable, water insoluble superabsorbent materials and the use of the superabsorbents in absorbent composites of absorbent articles.

Absorbent composites of absorbent articles typically contain superabsorbent material, in relatively high quantities in some cases, in various forms such as superabsorbent fibers and/or superabsorbent particles, homogeneously mixed with a matrix material, such as cellulose fluff pulp. The mixture of superabsorbent material and cellulose fluff pulp may be homogeneous throughout the absorbent composite or the superabsorbent material may be strategically located within the absorbent composite, such as forming a gradient within the fiber matrix. For example, more superabsorbent material may be present at one end of the absorbent composite than at an opposite end of the absorbent composite. Alternatively, more superabsorbent material may be present along a top surface of the absorbent composite than along a bottom surface of the absorbent composite or more superabsorbent material may be present along the bottom surface of the absorbent composite than along the top surface of the absorbent composite. One skilled in the art will appreciate the various embodiments available for absorbent composites. The water swellable, water insoluble superabsorbent materials of the present invention may be used in these and other various embodiments of absorbent composites.

Absorbent composites typically include a matrix which contains the superabsorbent material. The matrix is often made from a fibrous material or foam material, but one skilled in the art will appreciate the various embodiments of the composite matrix. One such fibrous matrix is made of a cellulose fluff pulp. The cellulose fluff pulp suitably includes wood pulp fluff. The cellulose pulp fluff may be exchanged, in whole or in part, with synthetic, polymeric fibers (e.g., meltblown fibers). Synthetic fibers are not required in the absorbent composites of the present invention, but may be included. One preferred type of wood pulp fluff is identified with the trade designation CR1654, available from Bowater, Childersburg, Ala., U.S.A., and is a bleached, highly absorbent wood pulp containing primarily soft wood fibers. The cellulose fluff pulp may be homogeneously mixed with the superabsorbent material. Within the absorbent article, the homogeneously mixed fluff and superabsorbent material may be selectively placed into desired zones of higher concentration to better contain and absorb body exudates. For example, the mass of the homogeneously mixed fluff and superabsorbent materials may be controllably positioned such that more basis weight is present in a front portion of the pad than in a back portion of the pad.

Absorbent composites of the present invention may suitably contain between about 5 to about 95 mass % of superabsorbent material, based on the total weight of the fiber, the superabsorbent material, and/or any other component. Optionally, the mass composition of the superabsorbent material in the absorbent composite may be from about 20 to about 80%. Additionally, the mass composition of the superabsorbent material in the absorbent composite may be from about 40 to about 60%.

Suitable superabsorbent materials useful in the present invention may be selected from natural, synthetic, and modified natural polymers and materials. The superabsorbent materials may be inorganic materials, such as silica gels, or organic compounds, including natural materials such as agar, pectin, guar gum, and the like, as well as synthetic materials, such as synthetic hydrogel polymers. Such hydrogel polymers include, for example, alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; polyamines; and, combinations thereof. Other suitable polymers include hydrolyzed acrylonitrile grafted starch, acrylic acid grafted starch, and isobutylene maleic anhydride copolymers and combinations thereof. The hydrogel polymers are suitably lightly crosslinked to render the material substantially water-insoluble. Crosslinking may, for example, be by irradiation or by covalent, ionic, Van der Waals, or hydrogen bonding. The superabsorbent materials of the present invention may be in any form suitable for use in absorbent structures, including, particles, fibers, flakes, spheres, and the like.

Typically, a superabsorbent polymer is capable of absorbing at least about 10 times its weight in a 0.9 weight percent aqueous sodium chloride solution, and particularly is capable of absorbing more than about 20 times its weight in 0.9 weight percent aqueous sodium chloride solution. Superabsorbent polymers suitable for treatment or modification in accordance with the present invention are available from various commercial vendors, such as Dow Chemical Company located in Midland, Mich., U.S.A., and Stockhausen Inc., Greensboro, N.C., USA. Other superabsorbent polymers suitable for treatment or modification in accordance with the present invention are described in U.S. Pat. No. 5,601,542 issued Feb. 11, 1997, to Melius et al.; U.S. patent application Ser. No. 09/475,829 filed in December 1999 and assigned to Kimberly-Clark Corporation; and, U.S. patent application Ser. No. 09/475,830 filed in December 1999 and assigned to Kimberly-Clark Corporation; each of which is hereby incorporated by reference in a manner consistent herewith.

Other examples of commercial superabsorbent materials that may be modified for use in the present invention include polyacrylate materials available from Stockhausen under the tradename FAVOR®. Examples include FAVOR® SXM 77, FAVOR® SXM 880, and FAVOR® SXM 9543. Other polyacrylate superabsorbent materials that may be modified for use in the present invention are available from Dow Chemical, USA under the tradename DRYTECH®, such as DRYTECH® 2035.

The superabsorbent materials of the present invention may be in the form of particles which, in the unswollen state, have maximum cross-sectional diameters typically within the range of from about 50 microns to about 1,000 microns, suitably within the range of from about 100 microns to about 800 microns, as determined by sieve analysis according to American Society for Testing Materials (ASTM) Test Method D-1921. It is understood that the particles of superabsorbent material, falling within the ranges described above, may include solid particles, porous particles, or may be agglomerated particles including many smaller particles agglomerated into particles within the described size ranges.

Absorbent composites may also contain any of a variety of chemical additives or treatments, fillers or other additives, such as clay, zeolites and/or other odor-absorbing material, for example activated carbon carrier particles or active particles such as zeolites and activated carbon. Absorbent composites may also include binding agents, such as crosslinkable binding agents or adhesives, and/or binder fibers, such as bicomponent fibers. Absorbent composites may or may not be wrapped or encompassed by a suitable tissue wrap that maintains the integrity and/or shape of the absorbent composite.

The structure and components of absorbent composites are designed to take up fluids and absorb them. The porosity of the fiber matrix allows fluid to penetrate the absorbent composite and contact the superabsorbent material, which absorbs the fluids. The superabsorbent material swells as the superabsorbent material absorbs fluids. The swelling of the superabsorbent material may be influenced by the external factors such as surrounding matrix material and pressures (i.e., a force per unit area, or stress) from the absorbent article user. The surrounding matrix fibers and/or superabsorbent materials and the pressures on the superabsorbent material may inhibit the swelling of the superabsorbent material, thus stopping absorbency, and thereby the absorbent composite, from reaching full free swell capacity. Also, as described above, stresses acting on an absorbent composite, such as an absorbent composite employing a superabsorbent material, may reduce porosity and/or permeability of the absorbent composite.

To the extent possible during swelling, superabsorbent materials may move within the composite matrix to positions that allow the superabsorbent to obtain greater swelling. Superabsorbent materials may rotate and/or translate so as to fit within voids in the composite matrix which allows the absorbent particle to swell readily against surrounding matrix and reach greater swelling potentials. Moreover, additional voids/void space may be created by overall expansion of the absorbent composite. Upon moving within the fiber matrix, the superabsorbent materials will contact and rub against other components of the absorbent composite, including matrix fibers and/or other superabsorbent materials. The surface mechanics of the superabsorbent material and the surrounding matrix components may determine the amount of superabsorbent material structure rotation and/or translation and thus may affect: (1) the swelling capacity of the superabsorbent material, and therefore the absorbent composite; and (2) the level of stress buildup in an absorbent composite employing the superabsorbent, which in turn affects the porosity and permeability of the absorbent composite.

The friction angle of the superabsorbent material is an important mechanical property that may affect the ability of the superabsorbent material to move or expand within the absorbent composite matrix. As discussed above in the Overview section, friction angle comes from Mohr-Coulomb failure theory, and the tangent of the friction angle is equivalent to the traditional coefficient of static friction. A smaller friction angle may indicate less contact friction between the superabsorbent material and the surrounding matrix, and a greater ability for the superabsorbent material to rearrange within the matrix during swelling so that the superabsorbent material may retain a greater portion of the free swell absorbent capacity. Also, a smaller friction angle may promote failure (i.e., movement between, for example, swollen particles of superabsorbent material; or movement between a swollen particle of superabsorbent material and the surrounding fiber matrix; etc.) at lower levels of stress buildup, thereby reducing losses in porosity and/or permeability in an absorbent composite.

Figure 7:
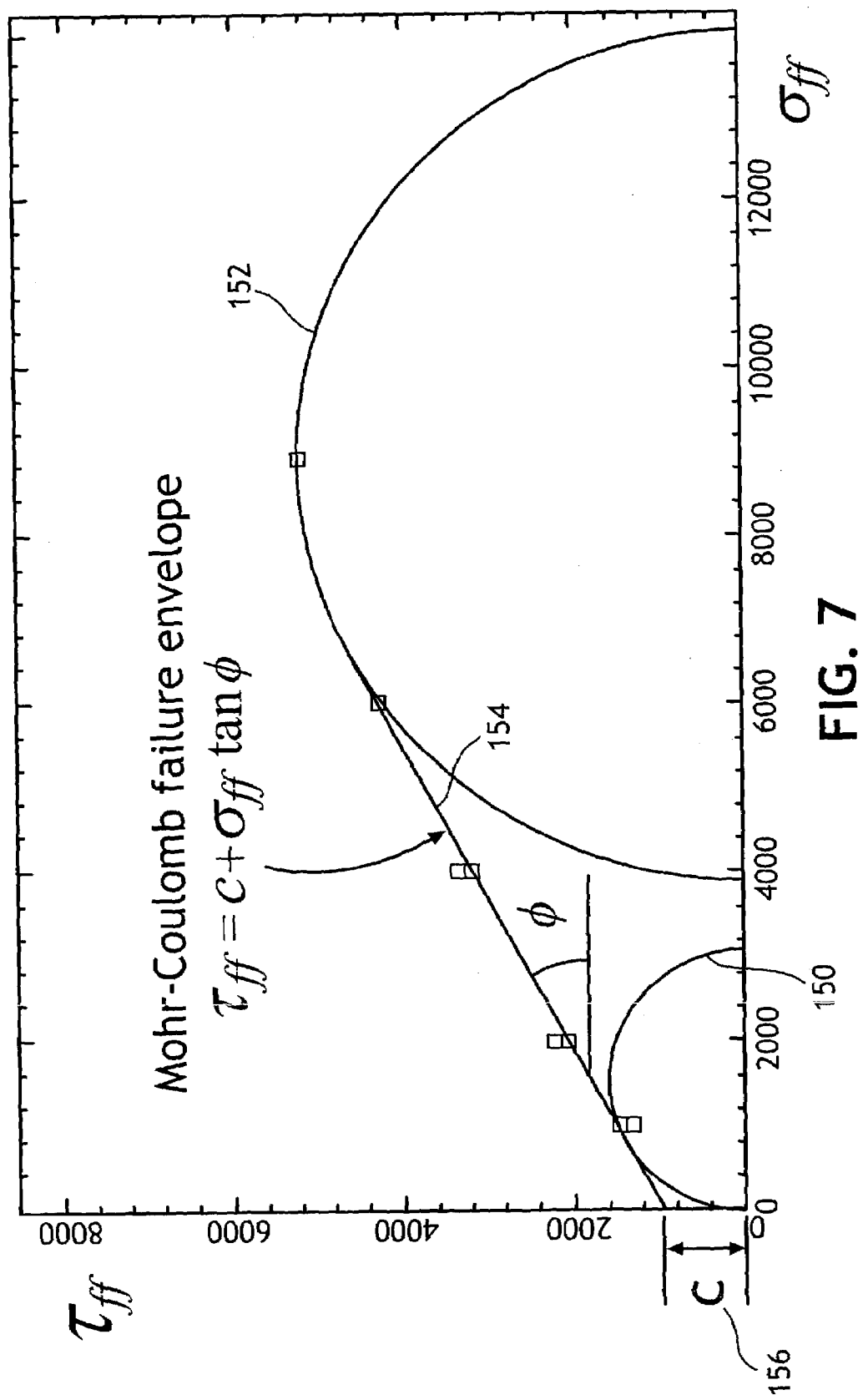
FIG. 7 shows a specific example of Mohr Circles in relation to a Mohr-Coulomb failure envelope on a plot of shear stress (y axis) versus normal stress (x axis).

The state of failure between the surfaces of the superabsorbent material and the surrounding components allows the superabsorbent material to rearrange within the wet matrix or a partially swollen gel-bed. As indicated in the Overview Section, Mohr circles may be used to describe the state of stress of a material, such as a wet gel-bed or absorbent composite or porous medium. FIG. 7 shows representative Mohr circles 150 and 152 for a typical gel-bed swollen to a particular level. FIG. 7 shows Mohr circles 150 and 152 for the superabsorbent FAVOR® 9543 at a 2.0 grams saline solution/gram superabsorbent material swelling level. The larger Mohr circle 152 represents a situation where some pre-consolidation stress is imposed on the gel-bed, and the smaller Mohr circle 150 represents the situation where some major principal stress exists anywhere in the gel-bed while the minor principle stress is zero. Although not shown in FIG. 7, Mohr circles are produced at each applied normal stress. The state of failure for a superabsorbent material is described by the set of Mohr circles at failure which together define a Mohr failure envelope. The Mohr failure envelope is often very close to linear, shown in FIG. 7 as line 154, and represents the shear stress at failure, on the failure plane, versus the normal stress acting on the same plane. The linearized failure envelope 154, often referred to as the Mohr-Coulomb failure criterion, may be represented mathematically by the formula:

$$\tau_{ff} = c + \sigma_{ff}(\tan \phi)$$

where $\tau_{ff}$ is shear stress, c is the effective cohesion constant, $\sigma_{ff}$ is normal stress, and $\phi$ is the friction angle of the gel-bed or superabsorbent material. The effective cohesion constant is represented on the graph by value 156 and pertains to the cohesion of the absorbent particle to the surrounding medium.

The gel-bed friction angle of the superabsorbent materials of the present invention may be determined using various methods used in fields such as soil mechanics. Useful instruments for determining gel-bed friction angle include triaxial shear measurement instruments, such as a Sigma1, available from GeoTac, Houston, Tex., or ring shear testers such as the Jenike-Shulze Ring Shear Tester, available from Jenike & Johanson, Westford, Mass.

Figure 8:
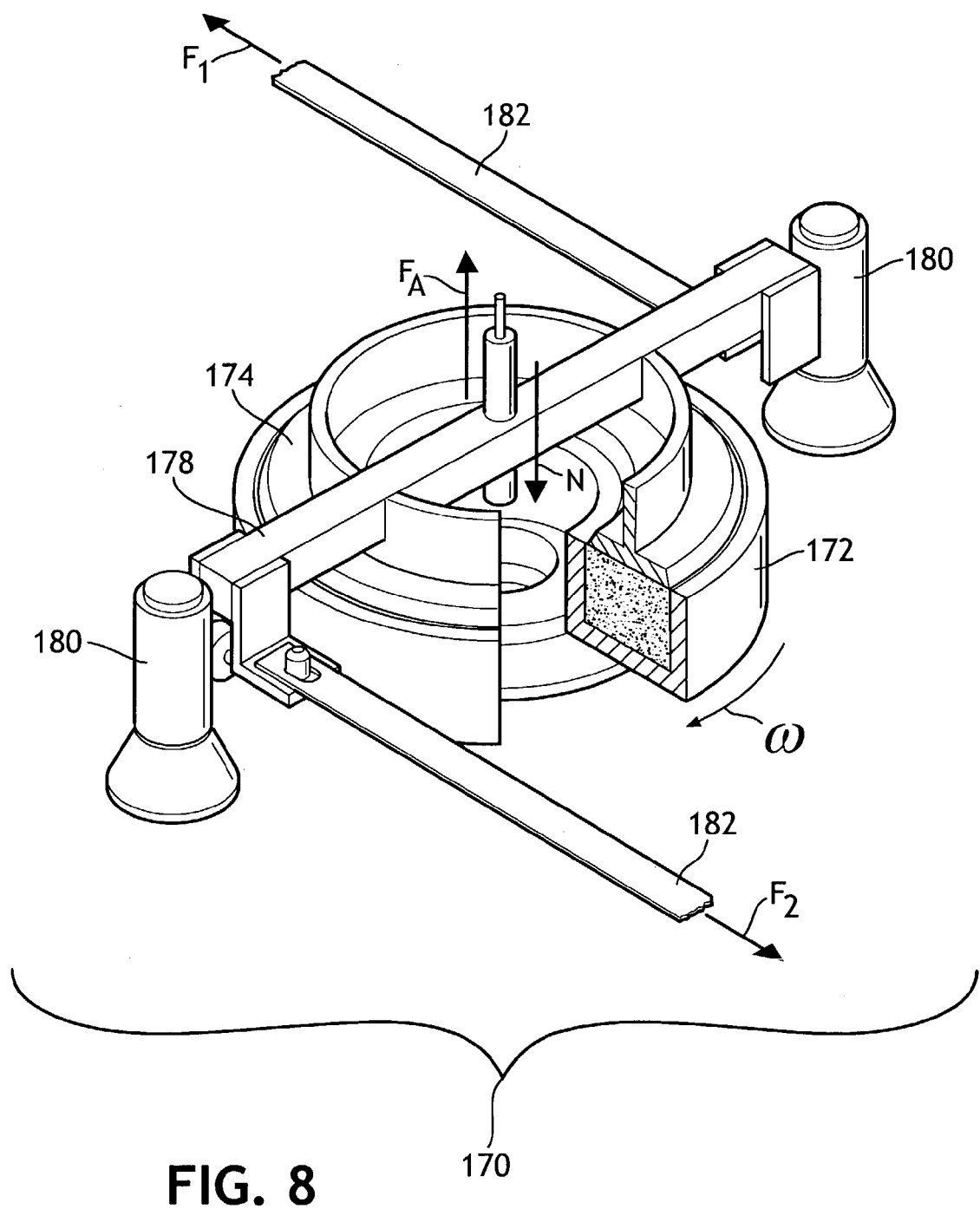
FIG. 8 shows an example of a friction-angle measuring device, in this case a Jenike-Schulze Ring-Shear Tester, available in the U.S. from Jenike & Johanson, Inc., a business having offices in Westford, Mass.

FIG. 8 shows a partial cut-away schematic of a Jenike-Shulze Ring Shear Tester, designated as reference numeral 170. The ring shear tester 170 has a ring shear cell 172 connected to a motor (not shown) that may rotate the ring shear cell 172 in direction ω. The ring shear cell 172 and lid 174 contain the superabsorbent material gel-bed 176 to be tested. The lid 174 is not fixed to the ring shear cell 172 and the crossbeam 178 crosses the lid 174 and connects two guiding rollers 180 and two tie rods 182 to lid 174. For measuring the gel-bed friction angle of swelled superabsorbent material gel-bed 176 the superabsorbent material is swelled outside the ring shear cell 172 and placed in the ring shear cell 172. A predetermined force N may be placed upon the lid 174, and therefore on the superabsorbent material 176, by a weight (not shown). A counterweight system (not shown) may be engaged to test at lower normal pressure. As the ring shear cell 172 rotates in direction ω by the computer controlled motor (not shown), a shear stress is placed on the superabsorbent material gel-bed 176 contacting the ring shear cell 172. An instrument connected to the tie rods 182 measures the forces F1 and F2, which are used to determine the shear stress at failure (for a given applied normal stress) of the superabsorbent material gel-bed 176.

Superabsorbent material having a low gel-bed friction angle may be useful in absorbent composites. In one embodiment of the present invention, the superabsorbent material gel-bed friction angle decreases upon swelling to about 20 degrees or less at a superabsorbent material swelling level of about 2.0 grams of 0.9 weight percent aqueous sodium chloride solution/gram of superabsorbent material (gram/gram) and remains at about 20 degrees or less at swelling levels greater than 2.0 gram/gram. More suitably the superabsorbent material gel-bed friction angle decreases upon swelling to about 15 degrees or less at a superabsorbent material swelling level of about 2.0 grams of 0.9 weight percent aqueous sodium chloride solution/gram of superabsorbent material and remains at about 15 degrees or less at swelling levels greater than 2.0 gram/gram. More particularly, the superabsorbent material gel-bed friction angle decreases upon swelling to about 10 degrees or less at a superabsorbent material swelling level of about 2.0 grams of 0.9 weight percent aqueous sodium chloride solution/gram of superabsorbent material, and remains at about 10 degrees or less at swelling levels greater than 2.0 gram/gram The low gel-bed friction angle superabsorbent materials of the present invention reduce the local stresses between the superabsorbent materials and/or the surrounding matrix components, which may allow the superabsorbent material structures to rearrange within the voids of an absorbent composite matrix more easily. The low gel-bed friction angle superabsorbent materials may allow for the superabsorbent materials to obtain a greater portion of their free swell absorbent capacity. In addition, permeability is generally maintained at suitable values because the development of higher internal stresses is alleviated. As indicated above, the buildup of stresses may result in additional compression of pore space.

Low superabsorbent material gel-bed friction angles may be obtained through non-conventional manufacturing processes that produce superabsorbent material structures possessing low-friction surfaces (e.g., smooth surfaces). Low superabsorbent material gel-bed friction angles may also be obtained by treatment of superabsorbent materials with friction angle reducing additives that decrease friction angle upon becoming wet. Examples of such friction angle reducing additives include, without limitation, glycerol, oils such as mineral oil and silicone oil, oleic acid, polysaccharides, polyethylene oxides.

The amount of gel-bed friction angle reducing additives, surfactants, or emulsifiers may be about 1.0% by weight of the swollen or unswollen superabsorbent material or less. Optionally, the amount of gel-bed friction angle reducing additives, surfactants, or emulsifiers may be about 10.0% by weight of the swollen or unswollen superabsorbent material or less. Additionally, the amount of gel-bed friction angle reducing additives, surfactants, or emulsifiers may be about 100.0% by weight of the swollen or unswollen superabsorbent material or less. The amount of gel-bed friction angle reducing additives, surfactants, or emulsifiers may be about 0.001% by weight of the swollen or unswollen superabsorbent material or greater. Optionally, the amount of gel-bed friction angle reducing additives, surfactants, or emulsifiers may be about 0.1% by weight of the swollen or unswollen superabsorbent material or greater. Additionally, the amount of gel-bed friction angle reducing additives, surfactants, or emulsifiers may be about 1.0% by weight of the swollen or unswollen superabsorbent material or greater.

Small concentrations of emulsifiers and/or surfactants in addition to the friction angle reducing additives, and friction angle reducing additive mixtures such as a 50/50 by weight mixture of glycerol and mineral oil, may help reduce the gel-bed friction angle of the superabsorbent materials. The emulsifiers and surfactants may increase the miscibility between nonpolar friction angle reducing additives, such as mineral oil, and polar friction angle reducing additives, such as glycerol. The emulsifiers and surfactants may also play an integral role in coating the swollen superabsorbent materials. Various emulsifiers and/or surfactants may be used in the present invention depending on the friction angle reducing additive used. Examples of emulsifiers are phosphatidylcholine and lecithin. Examples of liquid surfactants include sorbitan monolaurate, compounds of the TRITON® series (X-100, X-405 & SP-135) available from J. T. Baker, compounds of the BRIJ® series (92 and 97) available from J. T. Baker, polyoxyethylene (80) sorbitan monolaurate, polyoxyethylene sorbitan tetraoleate, and triethanolamine and other alcohol amines, and combinations thereof. When using mixtures of polar and nonpolar compounds, such as friction angle or cohesion value altering additives, emulsifiers, and surfactants, the nonpolar compound may be present in a larger proportion than the polar compound.

Absorbent composites of the present invention may include various controlled gel-bed friction angle superabsorbent materials of the present invention, including superabsorbent materials having low gel-bed friction angles. The superabsorbent materials with controlled gel-bed friction angles may be homogeneously mixed within the absorbent composite or strategically located within different absorbent composite areas, where the respective controlled gel-bed friction angles are desired.

In one embodiment of the present invention, the gel-bed friction angle of the superabsorbent material decreases upon swelling to a first friction angle of about 20 degrees or less at a superabsorbent material swelling level of about 2.0 grams of 0.9 weight percent aqueous sodium chloride solution/gram of superabsorbent material, and the gel-bed friction angles may increase as the swelling level increases. More suitably, the gel-bed friction angle of the superabsorbent material decreases upon swelling to a first friction angle of about 15 degrees or less at a superabsorbent material swelling level of about 2.0 grams of 0.9 weight percent aqueous sodium chloride solution/gram of superabsorbent material, and the gel-bed friction angles may increase as the swelling level increases. More particularly, the gel-bed friction angle of the superabsorbent material decreases upon swelling to a first friction angle of about 10 degrees or less at a superabsorbent material swelling level of about 2.0 grams of 0.9 weight percent aqueous sodium chloride solution/gram of superabsorbent material, and the gel-bed friction angles may increase as the swelling level increases.

Low superabsorbent material gel-bed friction angles at lower swelling levels followed by high superabsorbent material gel-bed friction angles at higher swelling levels combines the advantages of the low gel-bed friction angles during the initial, early stages of swelling, allowing for the desired failure and rearrangement of the superabsorbent materials, with the advantages of the high gel-bed friction angles, additional support for maintaining composite integrity and permeability. Thus the superabsorbent material may obtain more of its free swell capacity and maintain desired absorbent composite porosity and permeability.

In one embodiment of the present invention, the gel-bed friction angle of the superabsorbent material (specifically, a superabsorbent material initially having a lower gel-bed friction angle, such as one or more of the low gel-bed friction angle superabsorbent materials described above) may be increased during swelling with a friction angle increasing additive that is located within the superabsorbent material structures in combination with the water swellable, water insoluble polymer. In one embodiment of the present invention, the friction angle increasing additive may be chitosan, which may create a sticky condition between anionic superabsorbent polymers, leading to a higher friction angle. Other examples of such friction angle increasing additives include, without limitation, sodium silicate, sodium aluminate, and alumino silicates.

The amount of gel-bed friction angle increasing additives, surfactants, or emulsifiers may be about 1.0% by weight of the swollen or unswollen superabsorbent material or less. Optionally, the amount of gel-bed friction angle increasing additives, surfactants, or emulsifiers may be about 10.0% by weight of the swollen or unswollen superabsorbent material or less. Additionally, the amount of gel-bed friction angle increasing additives, surfactants, or emulsifiers may be about 100.0% by weight of the swollen or unswollen superabsorbent material or less. The amount of gel-bed friction angle increasing additives, surfactants, or emulsifiers may be about 0.001% by weight of the swollen or unswollen superabsorbent material or greater. Optionally, the amount of gel-bed friction angle increasing additives, surfactants, or emulsifiers may be about 0.1% by weight of the swollen or unswollen superabsorbent material or greater. Additionally, the amount of gel-bed friction angle increasing additives, surfactants, or emulsifiers may be about 1.0% by weight of the swollen or unswollen superabsorbent material or greater.

The friction angle increasing additive may have a tendency to migrate from within the polymer structure to the surface of the superabsorbent material as the superabsorbent material swells. In effect, the friction angle increasing additive may not coat, or substantially coat, the superabsorbent material surface when dry and, upon wetting, it migrates to the surface during swelling, thereby causing the gel-bed friction angle of the superabsorbent material to increase. The friction angle increasing additives may be organic and/or inorganic additives, either natural or synthetic.

Small concentrations of emulsifiers and/or surfactants may be used in addition to the friction angle increasing additives, and friction angle increasing additive mixtures, may help increase the gel-bed friction angle of the superabsorbent materials. The emulsifiers and surfactants may increase the miscibility between nonpolar friction angle increasing additives and polar friction angle increasing additives. The emulsifiers and surfactants may also play an integral role in coating the swollen superabsorbent materials. Various emulsifiers and/or surfactants may be used in the present invention depending on the friction angle increasing additive used. Examples of emulsifiers are phosphatidylcholine and lecithin. Examples of liquid surfactants include sorbitan monolaurate, compounds of the TRITON® series (X-100, X-405 & SP-135) available from J. T. Baker, compounds of the BRIJ® series (92 and 97) available from J. T. Baker, polyoxyethylene (80) sorbitan monolaurate, polyoxyethylene sorbitan tetraoleate, and triethanolamine and other alcohol amines, and combinations thereof.

In another embodiment of the present invention, the gel-bed friction angle of the superabsorbent material (specifically, a superabsorbent material initially having a lower gel-bed friction angle, such as one or more of the low gel-bed friction angle superabsorbent materials described above) may be increased with a friction angle increasing additive located within the matrix of the absorbent composite. The friction angle increasing additive is in combination with a matrix component, such as coated onto the wettable matrix fibers. The friction angle increasing additive has a tendency to release from the fibers upon wetting and associate with the surface of the superabsorbent material to increase the gel-bed friction angle of the superabsorbent material. Suitably, the friction angle increasing additive debonds with the matrix component at a controlled rate upon wetting, and thereby gradually increases the gel-bed friction angle of the superabsorbent material over a desired time period. The friction angle increasing additives may be organic and/or inorganic additives, natural and/or synthetic materials.

The additives, such as the friction angle increasing additives and friction angle reducing additives, which may alter the friction angle of superabsorbent materials, may be delivered either directly or indirectly to the superabsorbent. Direct delivery could occur through release from the superabsorbent material itself while indirect delivery could occur from fiber or some other component positioned within or adjacent the superabsorbent material and/or the absorbent composite. Furthermore, friction angle altering additives may be delivered gradually over some time period through release from any of the existing components present in the absorbent composite or as the result of some chemical reaction devised to release the friction angle altering additive at the most desirable moment. For example, the friction angle altering additive may be attached to the surface of the superabsorbent material or embedded within its interior, or it may be loaded onto and/or into some other component present in the absorbent composite, including but not limited to the fibrous material. The friction angle altering additive may be available immediately, leading to immediate alteration of the friction angle, or because of a chemical reaction or diffusion or some other mechanism, gradually alter the friction angle in the desired manner at some desired time.

It may be desirable to treat the superabsorbent material, the fiber and/or fibrous matrix, and/or other components that may be used in an absorbent composite with a friction angle altering additive, such as the friction angle reducing additive, the friction angle increasing additive and/or combinations thereof, to provide materials having desired initial friction angles. The material treated with the friction angle altering additive to provide a desired initial friction angle may then be treated with additional friction angle altering additives in accordance with the present invention. The term "substantially" when used herein in regard with friction angle, means within +/− one degree. The term "substantially" when used herein in regard with cohesion value, means within +/−100 Pascals.

The controlled gel-bed friction angle superabsorbent materials of the present invention may be incorporated into absorbent composites useful in absorbent articles. The various controlled gel-bed friction angle superabsorbent materials of the present invention may be used in various composite structures known in the art, such as described above, including fibrous composites such as meltblown, airlaid, and spunbond composites and foam composites. The superabsorbent materials of the present invention may be formed in various structures in absorbent composites, including particles, flakes, fibers, and spheres.

In accordance with one embodiment of the present invention, a superabsorbent material may comprise a water swellable, water insoluble superabsorbent material. The superabsorbent material may have a first gel-bed friction angle at a superabsorbent material swelling level of about 2.0 grams of 0.9 weight percent sodium chloride solution/gram of the superabsorbent material. The superabsorbent material also may have gel-bed friction angles, at superabsorbent material swelling levels greater than about 2.0 grams of 0.9 weight percent sodium chloride solution/gram of the superabsorbent material, substantially equal to or less than the first gel-bed friction angle. The first gel-bed friction angle may be about 20 degrees or less.

In accordance with other aspects of the present invention, the first gel-bed friction angle may be about 10 degrees or less. The water swellable, water insoluble superabsorbent material may be selected from the group consisting essentially of natural materials, modified natural materials, synthetic materials, and combinations thereof. The superabsorbent material may further comprise a structure selected from the group consisting of particles, fibers, flakes, spheres, and combinations thereof.

The water swellable, water insoluble superabsorbent material may be selected from the group consisting essentially of natural materials, modified natural materials, synthetic materials, and combinations thereof. The water swellable, water insoluble superabsorbent material may be selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

The present invention may further comprise a friction angle reducing additive in combination with the superabsorbent material. The friction angle reducing additive may be selected from the group consisting essentially of glycerol, mineral oil, silicone oil, polysaccharides, polyethylene oxides, and combinations thereof. The superabsorbent material may further comprise an emulsifier in combination with the superabsorbent material. The emulsifier may be selected from the group consisting essentially of phosphatidylcholine, lecithin, and combinations thereof. The superabsorbent material may further comprise a surfactant in combination with the superabsorbent material. The surfactant may be selected from the group consisting essentially of sorbitan monolaurate, compounds of the Triton series, compounds of the Brij series, polyoxyethylene sorbitan monolaurate, polyoxyethylene sorbitan tetraoleate, alcohol amines, and combinations thereof.

In accordance with another embodiment of the present invention, a superabsorbent material may comprise a water swellable, water insoluble superabsorbent material. The superabsorbent material may have a first gel-bed friction angle at a superabsorbent material swelling level of about 2.0 grams of 0.9 weight percent sodium chloride solution/gram of the superabsorbent material. The superabsorbent also may have gel-bed friction angles, at superabsorbent material swelling levels greater than about 2.0 grams of 0.9 weight percent sodium chloride solution/gram of the superabsorbent material, greater than the first gel-bed friction angle. The first gel-bed friction angle may be about 20 degrees or less.

In accordance with other aspects of the present invention, the first gel-bed friction angle may be about 10 degrees or less. The superabsorbent material may further comprise a friction angle increasing additive within the superabsorbent material in combination with the water swellable, water insoluble superabsorbent material. The friction angle increasing additive is selected from the group consisting essentially of chitosan, sodium silicate, sodium aluminate, alumino silicates, and combinations thereof.

The water swellable, water insoluble superabsorbent material may be selected from the group consisting essentially of natural materials, modified natural materials, synthetic materials, and combinations thereof. The superabsorbent material may further comprise a structure selected from the group consisting of particles, fibers, flakes, spheres, and combinations thereof.

The water swellable, water insoluble superabsorbent material may be selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

In accordance with another embodiment of the present invention, an absorbent composite may comprise a water swellable, water insoluble superabsorbent material and a plurality of wettable fibers. The water swellable, water insoluble superabsorbent material in combination with the wettable fibers may have a first gel-bed friction angle at a superabsorbent material swelling level of about 2.0 grams of 0.9 weight percent sodium chloride solution/gram of the superabsorbent material. The superabsorbent material also may have gel-bed friction angles at superabsorbent material swelling levels greater than about 2.0 grams of 0.9 weight percent sodium chloride solution/gram of the superabsorbent material, substantially equal to or less than the first gel-bed friction angle. The first gel-bed friction angle may be about 20 degrees or less.

In accordance with other aspects of the present invention, the first gel-bed friction angle may be about 10 degrees or less. The superabsorbent material may further comprise a structure selected from the group consisting of particles, fibers, flakes, spheres, and combinations thereof.

The water swellable, water insoluble superabsorbent material may be selected from the group consisting essentially of natural materials, modified natural materials, synthetic materials, and combinations thereof. The water swellable, water insoluble superabsorbent material may be selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

The present invention may further comprise a friction angle reducing additive in combination with the superabsorbent material. The friction angle reducing additive may be selected from the group consisting essentially of glycerol, mineral oil, silicone oil, polysaccharides, polyethylene oxides, and combinations thereof. The superabsorbent material may further comprise an emulsifier in combination with the superabsorbent material. The emulsifier may be selected from the group consisting essentially of phosphatidylcholine, lecithin, and combinations thereof. The superabsorbent material may further comprise a surfactant in combination with the superabsorbent material. The surfactant may be selected from the group consisting essentially of sorbitan monolaurate, compounds of the Triton series, compounds of the Brij series, polyoxyethylene sorbitan monolaurate, polyoxyethylene sorbitan tetraoleate, alcohol amines, and combinations thereof.

The present invention may further comprise a friction angle reducing additive in combination with the wettable fibers. The wettable fibers may be selected from the group consisting essentially of natural fibers, synthetic fibers, and combinations thereof.

In accordance with another embodiment of the present invention, an absorbent composite may comprise a water swellable, water insoluble superabsorbent material and a plurality of wettable fibers. The water swellable, water insoluble superabsorbent material in combination with the wettable fibers may have a first gel-bed friction angle at a superabsorbent material swelling level of about 2.0 grams of 0.9 weight percent sodium chloride solution/gram of the superabsorbent material. The water swellable, water insoluble superabsorbent material also may have gel-bed friction angles, at superabsorbent material swelling levels greater than about 2.0 grams of 0.9 weight percent sodium chloride solution/gram of the superabsorbent material, greater than the first gel-bed friction angle. The first gel-bed friction angle may be about 20 degrees or less. In the alternative, the first gel-bed friction angle may be about 10 degrees or less.

The present invention may further comprise a friction angle increasing additive in combination with the water swellable, water insoluble superabsorbent material. In the alternative, the friction angle increasing additive may be in combination with the wettable fibers. The friction angle increasing additive may be selected from the group consisting essentially of chitosan, sodium silicate, sodium aluminate, alumino silicates, and combinations thereof. The wettable fibers may be selected from the group consisting essentially of natural fibers, synthetic fibers, and combinations thereof.

The water swellable, water insoluble superabsorbent material is selected from the group consisting essentially of natural materials, modified natural materials, synthetic materials, and combinations thereof. The water swellable, water insoluble superabsorbent material may be selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

In accordance with another embodiment of the present invention, a superabsorbent material may comprise a water swellable, water insoluble superabsorbent material. The superabsorbent material may have a first gel-bed friction angle at a first superabsorbent material swelling level of the superabsorbent material and gel-bed friction angles, at superabsorbent material swelling levels greater than the first superabsorbent material swelling level of the superabsorbent material. The gel-bed friction angles may be greater than the first gel-bed friction angle. The first gel-bed friction angle may be about 20 degrees or less. In the alternative, the first gel-bed friction angle may be 10 degrees or less.

In accordance with other aspects of the present invention, the superabsorbent material may further comprise a friction angle increasing additive within the superabsorbent material in combination with the water swellable, water insoluble superabsorbent material. The friction angle increasing additive may be selected from the group consisting essentially of chitosan, sodium silicate, sodium aluminate, alumino silicates, and combinations thereof. The water swellable, water insoluble superabsorbent material may be selected from the group consisting essentially of natural materials, modified natural materials, synthetic materials, and combinations thereof.

The water swellable, water insoluble superabsorbent material may be selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof. The superabsorbent material may further comprise a structure selected from the group consisting essentially of particles, fibers, flakes, spheres, and combinations thereof.

In accordance with another embodiment of the present invention, an absorbent composite may comprise a plurality of wettable fibers and a water swellable, water insoluble superabsorbent material in combination with the wettable fibers. The water swellable, water insoluble superabsorbent material may have a first gel-bed friction angle at a first superabsorbent material swelling level of the superabsorbent material and gel-bed friction angles, at superabsorbent material swelling levels greater than the first superabsorbent material swelling level of the superabsorbent material, greater than the first gel-bed friction angle. The first gel-bed friction angle may be about 20 degrees or less. In the alternative, the first gel-bed friction angle may be about 10 degrees or less.

In accordance with other aspects of the present invention, the absorbent composite may further comprise a friction angle increasing additive in combination with the water swellable, water insoluble superabsorbent material. The absorbent composite may further comprise a friction angle increasing additive in combination with the wettable fibers. The friction angle increasing additive may be selected from the group consisting essentially of chitosan, sodium silicate, sodium aluminate, alumino silicates, and combinations thereof. The plurality of wettable fibers may be selected from the group consisting essentially of natural fibers, synthetic fibers, and combinations thereof. The water swellable, water insoluble superabsorbent material may be selected from the group consisting essentially of natural materials, modified natural materials, synthetic materials, and combinations thereof.

Friction Angle Determination

A ring shear testing device such as a Jenike-Schulze Ring Shear Tester apparatus may be used to determine a superabsorbent material gel-bed friction angle. For testing, a sufficient amount (200-1000 grams) of swollen superabsorbent material (e.g., swollen 0-30 g/g or more) is placed within the ring shear cell. For the samples described below, the standard procedure for determining 'yield locus' as described in the manuals 'RST-01.pc, RST-CONTROL' for the Jenike-Shulze Ring shear tester was followed. The specific details for the material preparation and test procedure are given below:

The superabsorbent material is swollen to the desired level by 0.9 weight percent aqueous sodium chloride (such as that available from Ricca Chemical Company, Arlington, Tex.) in a Kitchen Aid™ blender (model #K5SS, 5 Quart); by first pouring a specific amount of the solution (200-1000 grams) in the blender bowl (bowl approximate volume: 5 quart) and then adding a predetermined quantity (22-600 grams) of dry superabsorbent material while the stirrer is slowly churning the fluid at the lowest speed setting (setting range 1-10, where 1 is the lowest and 10 is the highest). This is done so as to distribute the swelling solution uniformly to all the superabsorbent material. When all solution is absorbed by the superabsorbent material (absorption time: 0-30 minutes), the bowl is removed from the blender, covered so as to prevent evaporation and allowed to equilibrate for one hour so that the fluid is distributed evenly throughout each particle. The sample is manually mixed every fifteen minutes to ensure that no clumps are formed.

| SAP Capacity (g/g) | SAP-Fluid Ratio | Dry Weight Needed (grams) | Saline Weight Needed (grams) | Total Weight SAP-Fluid (grams) | Amount for standard Ring-Cell (grams) |
|---|---|---|---|---|---|
| 1 | 1:1 | 250 | 250 | 500 | 350-450 |
| 2 | 1:2 | 150 | 300 | 450 | 350-450 |
| 5 | 1:5 | 80 | 400 | 480 | 400-480 |
| 10 | 1:10 | 50 | 500 | 550 | 450-550 |
| 15 | 1:15 | 40 | 600 | 640 | 540-640 |
| 20 | 1:20 | 30 | 600 | 630 | 550-630 |

If a coating is applied to the superabsorbent material, the appropriate coating additive is prepared separately, for example, as described below. The equilibrated (time approximately: 1 hour) and swollen superabsorbent material is coated evenly using a Kitchen Aid™ blender by first introducing the swollen superabsorbent material into the bowl, and then slowly adding the coating additive (addition time: 1-30 minutes) while turning the superabsorbent material in the bowl at the lowest speed setting (setting range 1-10, where 1 is the lowest and 10 is the highest) with the stirrer at all times. The coated superabsorbent material is allowed to rest for 0-30 minutes with manual mixing every five minutes to maintain equal distribution of treatment.

The gel-bed friction angle and effective cohesion measurements are determined by using the Jenike-Schulze Ring Shear Tester apparatus. The Jenike-Schulze Ring Shear Tester is used to obtain the gel-bed friction angle values of superabsorbent material gel-beds at various swelling levels. The Ring Shear Tester is operated and calibrated according to the manufacturer's instructions provided. A sample is loaded into the ring shear cell (Volume Ring Cell—standard: 942.48 cm$^3$) while ensuring the superabsorbent gel-bed is distributed evenly (see above table). After one hour of assumed equilibration with 0.9 weight percent sodium chloride solution is achieved, the ring shear cell is filled with the bulk superabsorbent material to be tested (see above table). Even filling may be obtained by removing excess material with a spatula, without compressing the superabsorbent material. The superabsorbent material gel-bed is suitably flush with the top of the ring shear cell. The weight of the filled ring shear cell (without the lid) is determined on a mass balance and recorded. The samples described below were tested by the ring shear tester control program (RSTCTRL) for 1-2 hours. On request from RSTCTRL, the filled shear cell is securely placed on the driving axle. The lid is placed on the ring shear cell and positioned a few degrees counterclockwise from the shear position; the ring shear tester pre-sets this start position. The handle of the counterweight should be on the right side of the crossbeam, and the hook on the crossbeam should be facing the handle. On request from RSTCTRL, the counter weight and the hanger are hooked to the central axis of the crossbeam. The tie rods are attached on each side of the crossbeam, and the ring shear cell is adjusted so that the tie rods are not stressed. The RST-Control offers the possibility to adjust the shear cell with arrow keys: ←→, and using: ↑↓ to stop when positioned properly.

During the test procedure, the pressures at which the sample is pre-sheared are read from a control file. In the sample tests described below, the pre-shearing normal pressure is set at 3000 Pascals and the pre-sheared/pre-consolidated gel-bed is then sheared to failure, to obtain the Mohr-Coulomb envelope, at a range of normal pressures ranging from 500 Pascals to 2500 Pascals. Pre-shearing precedes each shearing measurement. Thus, every superabsorbent material gel-bed is sheared twice at any shearing normal pressure in one experiment. Sometimes the equipment needs to be run in semiautomatic mode and the data point is obtained manually. After the samples below were completed, the results were analyzed using RSV 95, Version 1.0; the software package included with the ring shear tester.

EXAMPLES

To demonstrate aspects of the present invention, superabsorbent material, designated as FAVOR® SXM 9543, available from Stockhausen, Inc., a business having offices in Greensboro, N.C., was treated to reduce the gel-bed friction angle.

Control

The gel-bed friction angle of the superabsorbent material, untreated FAVOR® SXM 9543, was measured as a control at various swelling levels. The results are summarized in Table 1.

TABLE 1

| Swelling level (gram/gram) | 2 | 5 | 10 | 15 | 20 |
|---|---|---|---|---|---|
| Gel-bed friction angle (degree) | 23 | 15 | 12 | 11 | 12 |

As a comparison with the FAVOR® SXM 9543 control, the gel-bed friction angle of the superabsorbent material DRYTECH® 2035 was also measured at various swelling levels. DRYTECH® 2035 is available from Dow Chemical Company, a business having offices in Midland, Mich. The results are summarized in Table 2.

TABLE 2

| Swelling level (gram/gram) | 2 | 5 | 10 | 15 |
|---|---|---|---|---|
| Gel-bed friction angle (degree) | 29 | 17 | 11 | 4 |

Sample 1

An amount of FAVOR® SXM 9543 was first swollen to a swelling level of 2 grams of 0.9 weight percent aqueous sodium chloride solution per gram of superabsorbent material (gram/gram), and equilibrated for one hour, as described above. A coating of glycerol, CAS 56-81-5 (99 percent minimum), available from J. T. Baker, a business having offices in Phillipsburg, N.J., in the ratio of 1.0 gram of additive per 2.0 grams of the swollen superabsorbent material was applied to the superabsorbent material. The gel-bed friction angle was measured as described above. The gel-bed friction angle of Sample 2 at the given swelling level was found to be 20 degrees and is summarized in Table 3.

Sample 2

An amount of FAVOR® SXM 9543 was first swollen to a desired swelling level of 2 gram of 0.9 weight percent of aqueous sodium chloride solution per gram of superabsorbent material, and equilibrated for one hour, as described above. A coating of mineral oil, CAS 8012-95-1 (white mineral oil with Vitamin E as a stabilizer), available from J. T. Baker, a business having offices in Phillipsburg, N.J., in the ratio of 1.0 gram of additive per 2.0 grams of the swollen superabsorbent material was applied to the superabsorbent material. The gel-bed friction angle was measured as described above. The gel-bed friction angle of the coated superabsorbent material at the given swelling level was found to be 6 degrees and is summarized in Table 3.

Sample 3

An amount of FAVOR® SXM 9543 was first swollen to a desired swelling level of 2 grams of 0.9 weight percent of aqueous sodium chloride solution per gram of superabsorbent material, and equilibrated for one hour, as described above. A coating of silicone oil, CAS 63148-62-9 (density 0.963 gram/cubic centimeter), available from Sigma Aldrich, a business having offices in St. Louis, Mo., in the ratio of 1.0 gram of additive per 2.0 grams of the swollen superabsorbent material was applied to the superabsorbent material. The gel-bed friction angle was measured as described above. The gel-bed friction angle of the coated superabsorbent material at the given swelling level was found to be 17 degrees and is summarized in Table 3.

Sample 4

An amount of FAVOR® SXM 9543 was first swollen to a desired swelling level of 2 grams of 0.9 weight percent of aqueous sodium chloride solution per gram of superabsorbent material, and equilibrated for one hour, as described above. A coating, of 50 percent by weight of mineral oil (from Sample 2) and 50 percent by weight of glycerol (from Sample 1), in the ratio of 1.0 gram of additive coating per 2.0 grams of the swollen superabsorbent material was applied to the superabsorbent material. The gel-bed friction angle was measured as described above. The gel-bed friction angle of the coated superabsorbent material at the given swelling level was found to be 11 degrees and is summarized in Table 3.

Sample 5

An amount of FAVOR® SXM 9543 was first swollen to a desired swelling level of 2 grams of 0.9 weight percent of aqueous sodium chloride solution per gram of superabsorbent material, and equilibrated for one hour, as described above. A coating, mineral oil (from Sample 2), glycerol (from Sample 1), and lecithin, CAS 8002-43-5 (dry, granular), available from Spectrum Quality Products, Inc., a business having offices in Gardena, Calif., in the ratio of 1.0 gram of additive/coating per 2.0 grams of the swollen superabsorbent material was applied to the superabsorbent material. The coating additive was a mixture containing 0.5 grams of glycerol and 0.5 grams of mineral oil for every 1.0 gram of additive mixture plus 0.01 grams lecithin per 2.0 gram of swollen superabsorbent material as an emulsifier. The lecithin was prepared by grinding it to a fine powder for ten minutes and wetting slightly with deionized water (about 2-3 milliliters) to aid in mixing with the additive mixture. The lecithin was then added to the additive mixture and mixed for about 30 minutes until a uniform color with no observable lecithin particles was obtained. The additive was then mixed into the superabsorbent material that was previously swollen and had been equilibrating for one hour. The additive mixture and the superabsorbent material were mixed for about two minutes until there was little or no additive mixture adhered to the side of the mixing bowl. The gel-bed friction angle was measured as described above. The gel-bed friction angle of the coated superabsorbent material at the given swelling level was found to be 7 degrees and is summarized in Table 3.

Sample 6

An amount of FAVOR® SXM 9543 was first swollen to a desired swelling level of 2 gram of 0.9 weight percent of aqueous sodium chloride solution per gram of superabsorbent material, and equilibrated for one hour, as described above. A coating, mineral oil (from Sample 2), glycerol (from Sample 1), and lecithin (from Sample 5), in the ratio of 1.0 gram of additive/coating per 2.0 grams of the swollen superabsorbent material was applied to the superabsorbent material. The coating additive was a mixture containing 0.2 grams of glycerol and 0.8 grams of mineral oil for every 1.0 gram of additive mixture plus 0.05 grams lecithin per 2.0 gram of swollen superabsorbent material as an emulsifier. The lecithin was prepared by grinding it to a fine powder for ten minutes and wetting slightly with deionized water (about 2-3 milliliters) to aid in mixing with the additive mixture. The lecithin was then added to the additive mixture and mixed for about 30 minutes until a uniform color with no observable lecithin particles was obtained. The additive was then mixed into the superabsorbent material that was previously swollen and had been equilibrating for one hour. The additive mixture and the superabsorbent material were mixed for about two minutes and there was little or no additive mixture adhered to the side of the mixing bowl. The gel-bed friction angle was measured as described above. The gel-bed friction angle of the coated superabsorbent material at the given swelling level was found to be 2 degrees and is summarized in Table 3.

Sample 7

An amount of FAVOR® SXM 9543 was first swollen to a desired swelling level of 2 grams of 0.9 weight percent of aqueous sodium chloride solution per gram of superabsorbent material, and equilibrated for one hour, as described above. A coating, mineral oil (from Sample 2), glycerol (from Sample 1), and sorbitan monolaurate, CAS 1338-39-2 (density 1.058 grams/cubic centimeter), from Aldrich, in a ratio of 1.0 gram of additive/coating per 2.0 grams of the swollen superabsorbent material, was applied to the superabsorbent material. The coating material/fluid was a mixture containing 0.5 grams of glycerol and 0.5 grams of mineral oil for every 1.0 gram of additive mixture plus 0.05 grams sorbitan monolaurate per 2.0 gram of swollen superabsorbent material as an emulsifier. The additive was then mixed into the superabsorbent material that was previously swollen and had been equilibrating for one hour. The additive mixture and the superabsorbent material were mixed for about two minutes and there was little or no additive mixture adhered to the side of the mixing bowl. The gel-bed friction angle was measured as described above. The gel-bed friction angle of the coated superabsorbent material at the given swelling level was found to be 2 degrees and is summarized in Table 3.

Sample 8

An amount of FAVOR® SXM 9543 was first swollen to a desired swelling level of 2 grams of 0.9 weight percent of aqueous sodium chloride solution per gram of superabsorbent material, and equilibrated for one hour, as described above. A coating of sorbitan monolaurate (from Sample 7) in the ratio of 1.0 gram of additive per 2.0 grams of the swollen superabsorbent material was applied to the superabsorbent material. The gel-bed friction angle was measured as described above. The gel-bed friction angle of the coated superabsorbent material at the given swelling level was found to be 2 degrees and is summarized in Table 3.

TABLE 3

| Example | Gel-bed friction angle (in degrees) at swelling level of 2.0 gram/gram |
|---|---|
| Control | 23 |
| Sample 1 | 20 |
| Sample 2 | 6 |
| Sample 3 | 17 |
| Sample 4 | 11 |
| Sample 5 | 7 |
| Sample 6 | 2 |
| Sample 7 | 2 |
| Sample 8 | 2 |

Sample 9

Three amounts of FAVOR® SXM 9543 were swollen to swelling levels of 2 grams, 5 grams, and 10 grams, respectively, of 0.9 weight percent of aqueous sodium chloride solution per gram of superabsorbent material and equilibrated for one hour, as described above. A coating, mineral oil (from Sample 2), glycerol (from Sample 1), and lecithin (from Sample 5), in the ratio of 1.0 gram of additive/coating per 2.0 grams of the swollen superabsorbent material was applied to each of the superabsorbent samples. The coating additive was a mixture containing 0.5 grams of glycerol and 0.5 grams of mineral oil for every 1.0 gram of additive mixture plus 0.01 grams lecithin per 2.0 gram of swollen superabsorbent material as an emulsifier. The lecithin was prepared by grinding it to a fine powder for ten minutes and wetting slightly with deionized water (about 2-3 milliliters) to aid in mixing with the additive mixture. The lecithin was then added to the additive mixture and mixed for about 30 minutes until a uniform color with no observable lecithin particles was obtained. The additive was then mixed with one of the superabsorbent samples that had been equilibrating for one hour. The additive mixture and the superabsorbent material were mixed for about two minutes and there was little or no additive mixture adhered to the side of the mixing bowl. The gel-bed friction angle for each of the swelling levels was measured as described above. The gel-bed friction angle of the coated superabsorbent material at each of the given swelling levels is listed in Table 4.

TABLE 4

| Superabsorbent material swelling level | Gel-bed friction angle (in degrees) |
|---|---|
| 2 grams/gram | 7 |
| 5 grams/gram | 6 |
| 10 grams/gram | 4 |

Sample 10

Three amounts of FAVOR® SXM 9543 were swollen to swelling levels of 2 grams, 5 grams, and 10 grams, respectively, of 0.9 weight percent of aqueous sodium chloride solution per gram of superabsorbent material, and equilibrated for one hour, as described above. A coating, mineral oil (from Sample 2), glycerol (from Sample 1), and sorbitan monolaurate, (from Sample 8), in a ratio of 1.0 gram of additive per 3.0 grams of the swollen superabsorbent material, was applied to each of the superabsorbent samples. The coating additive was a mixture containing 0.2 grams of glycerol and 0.8 grams of mineral oil for every 1.0 gram of additive mixture plus 0.02 grams sorbitan monolaurate per 2.0 gram of swollen superabsorbent material as an emulsifier. The additive was then mixed into each of the superabsorbent samples that had been equilibrating for one hour. The additive mixture and the superabsorbent material were mixed for about two minutes and there was little or no additive mixture adhered to the side of the mixing bowl. The gel-bed friction angle was measured as described above. The gel-bed friction angle of the coated superabsorbent material at each of the given swelling levels is listed in Table 5.

TABLE 5

| Superabsorbent material swelling level | Gel-bed friction angle (in degrees) |
|---|---|
| 2 grams/gram | 5 |
| 5 grams/gram | 4 |
| 10 grams/gram | 4 |

Sample 11

An amount of FAVOR® SXM 9543 was first swollen to a desired swelling level of 2 grams of 0.9 weight percent of aqueous NaCl solution per gram of dry superabsorbent material, and equilibrated for one hour, as stated above. The first coating material of mineral oil (from Sample 2), glycerol (from Sample 1), and lecithin (from Sample 5) in a ratio of 1.0 gram additive/coating per 2.0 gram of swollen superabsorbent material was applied to the swollen superabsorbent. The first coating material was a mixture of 0.495 grams mineral oil, 0.495 grams glycerol, and 0.01 grams Lecithin per 1.0 gram additive/coating. The additive mixture and the superabsorbent material were mixed and set aside to equilibrate for 30 minutes. Half of the material was used to measure the gel-bed friction angle using the procedure as described above and the other half was set aside for further treatment. The first treatment gel-bed friction angle of the superabsorbent at the given swelling level was found to be 15 degrees. The second half of treated superabsorbent, that was previously set aside, was swollen to a second swelling level of 10 grams of 0.9 weight percent of aqueous NaCl solution per gram of dry superabsorbent material, and equilibrated for one hour. A second coating was applied to the treated swollen superabsorbent. The second coating material of sodium silicate solution, available from Aldrich, a business having offices in Milwaukee, Wis., in the ratio of 0.05 gram of additive per 1.0 gram of swollen superabsorbent material was applied to the swollen superabsorbent. The additive and the superabsorbent material were mixed and set aside to equilibrate for 30 minutes. The treated superabsorbent material was tested for gel-bed friction angle as described above. The second treatment gel-bed friction angle of the superabsorbent at the given swelling level of 10 gram per gram was found to be 28 degrees, higher than what was measured at 2 gram per gram.

Sample 12

Three amounts of FAVOR® SXM 9543 were swollen to swelling levels of 2 grams, 5 grams, and 10 grams, respectively, of 0.9 weight percent of aqueous NaCl solution per gram of dry superabsorbent material and equilibrated for one hour, as stated above. A coating material of glycerol (from Sample 1) in a ratio of 1.0 gram additive/coating per 2.0 gram of swollen superabsorbent material was applied to each of the swollen superabsorbent samples. The gel-bed friction angle for each of the swelling levels was measured as described above. The gel-bed friction angle of the coated superabsorbent material at each of the given swelling levels is listed in Table 6.

TABLE 6

| Superabsorbent material swelling level | Gel-bed friction angle (in degrees) |
|---|---|
| 2 grams/gram | 20 |
| 5 grams/gram | 15 |
| 10 grams/gram | 14 |

Sample 13

Three amounts of FAVOR® SXM 9543 were swollen to swelling levels of 2 grams, 5 grams, and 10 grams, respectively, of 0.9 weight percent of aqueous NaCl solution per gram of dry superabsorbent material and equilibrated for one hour, as stated above. A coating material of mineral oil, (from Sample 2), glycerol (from Sample 1), and sorbitan monolaurate (from Sample 7) in a ratio of 1.0 gram additive/coating per 2.0 gram of swollen superabsorbent material was applied to each of the swollen superabsorbent samples. The coating additive was a mixture containing 0.8 grams of glycerol and 0.2 grams of mineral oil for every 1.0 grams of additive mixture plus 0.01 grams of sorbitan monolaurate per 1.0 grams of swollen superabsorbent material. The additive was then mixed into the superabsorbent material (previously swollen) for about 2 minutes and there was little or no additive mixture adhered to the side of the mixing bowl. The gel-bed friction angle for each of the swelling levels was measured as described above. The gel-bed friction angle of the coated superabsorbent material at each of the given swelling levels is listed in Table 7.

TABLE 7

| Superabsorbent material swelling level | Gel-bed friction angle (in degrees) |
|---|---|
| 2 grams/gram | 16 |
| 5 grams/gram | 12 |
| 10 grams/gram | 4 |

Sample 14

An amount of FAVOR® SXM 9543 was first swollen to a desired swelling level of 2 grams of 0.9 weight percent of aqueous NaCl solution per gram of dry superabsorbent material, and equilibrated for one hour, as stated above. A coating of glycerol (from Sample 2) in the ratio of 1.0 gram of additive per 2.0 grams of the swollen superabsorbent material was applied to the swollen superabsorbent material. The coated and swollen superabsorbent material was dried in an oven at 90 degrees Celsius for 24 hours to remove swelling fluid. The oven dried coated superabsorbent material was re-swollen to a desired level of 2 grams of 0.9 weight percent of aqueous NaCl solution per gram of coated superabsorbent. The re-swollen superabsorbent material was tested for gel-bed friction angle as described above. The gel-bed friction angle of the superabsorbent at the given swelling level of 2 gram per gram was found to be 12 degrees.

Sample 15

An amount of FAVOR® SXM 9543 was first swollen to a desired swelling level of 10 grams of 0.9 weight percent of aqueous NaCl solution per gram of dry superabsorbent material, and equilibrated for one hour, as stated above. A coating of glycerol (from Sample 2) in the ratio of 1.0 gram of additive per 2.0 grams of the swollen superabsorbent material was applied to the swollen superabsorbent material. The coated and swollen superabsorbent material was dried in an oven at 60 degrees Celsius for 5 days to remove the swelling fluid. The oven dried coated superabsorbent material was re-swollen to a desired level of 2 grams of 0.9 weight percent of aqueous NaCl solution per gram of coated superabsorbent. The re-swollen superabsorbent material was tested for gel-bed friction angle as described above. The gel-bed friction angle of the superabsorbent at the given swelling level of 2 gram per gram was found to be 8 degrees.

While the embodiments of the present invention described herein are presently preferred, various modifications and improvements may be made without departing from the spirit and scope of the present invention. The scope of the present invention is indicated by the appended claims, and all changes that fall within the meaning and range of equivalents are intended to be embraced therein.

We claim:

1. A superabsorbent material, comprising:
a water swellable, water insoluble superabsorbent material; and,
the superabsorbent material having a first gel-bed friction angle at a superabsorbent material swelling level of about 2.0 grams of 0.9 weight percent sodium chloride solution/gram of the superabsorbent material and gel-bed friction angles, at superabsorbent material swelling levels greater than about 2.0 grams of 0.9 weight percent sodium chloride solution/gram of the superabsorbent material, substantially equal to or less than the first gel-bed friction angle,
wherein the first gel-bed friction angle is about 20 degrees or less.

2. The superabsorbent material of claim 1, wherein the first gel-bed friction angle is about 10 degrees or less.

3. The superabsorbent material of claim 1, wherein the water swellable, water insoluble superabsorbent material is selected from the group consisting essentially of natural materials, modified natural materials, synthetic materials, and combinations thereof.

4. The superabsorbent material of claim 3, wherein the water swellable, water insoluble superabsorbent material is selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

5. The superabsorbent material of claim 1, further comprising a friction angle reducing additive in combination with the superabsorbent material.

6. The superabsorbent material of claim 5, wherein the friction angle reducing additive is selected from the group consisting essentially of glycerol, mineral oil, silicone oil, polysaccharides, polyethylene oxides, and combinations thereof.

7. The superabsorbent material of claim 5, further comprising an emulsifier in combination with the superabsorbent material.

8. The superabsorbent material of claim 7, wherein the emulsifier is selected from the group consisting essentially of phosphatidylcholine, lecithin, and combinations thereof.

9. The superabsorbent material of claim 5, further comprising a surfactant in combination with the superabsorbent material.

10. The superabsorbent material of claim 9, wherein the surfactant is selected from the group consisting essentially of sorbitan monolaurate, compounds of the Triton series, compounds of the Brij series, polyoxyethylene sorbitan monolaurate, polyoxyethylene sorbitan tetraoleate, alcohol amines, and combinations thereof.

11. The superabsorbent material of claim 1, further comprising a structure selected from the group consisting essentially of particles, fibers, flakes, spheres, and combinations thereof.

12. A superabsorbent material, comprising:
a water swellable, water insoluble superabsorbent material; and,
the superabsorbent material having a first gel-bed friction angle at a superabsorbent material swelling level of about 2.0 grams of 0.9 weight percent sodium chloride solution/gram of the superabsorbent material and gel-bed friction angles, at superabsorbent material swelling levels greater than about 2.0 grams of 0.9 weight percent sodium chloride solution/gram of the superabsorbent material, greater than the first gel-bed friction angle,
wherein the first gel-bed friction angle is about 20 degrees or less.

13. The superabsorbent material of claim 12, wherein the first gel-bed friction angle is 10 degrees or less.

14. The superabsorbent material of claim 12, further comprising a friction angle increasing additive within the superabsorbent material in combination with the water swellable, water insoluble superabsorbent material.

15. The superabsorbent material of claim 14, wherein the friction angle increasing additive is selected from the group consisting essentially of chitosan, sodium silicate, sodium aluminate, alumino silicates, and combinations thereof.

16. The superabsorbent material of claim 12, wherein the water swellable, water insoluble superabsorbent material is selected from the group consisting essentially of natural materials, modified natural materials, synthetic materials, and combinations thereof.

17. The superabsorbent material of claim 16, wherein the water swellable, water insoluble superabsorbent material is selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

18. The superabsorbent material of claim 12, further comprising a structure selected from the group consisting essentially of particles, fibers, flakes, spheres, and combinations thereof.

19. An absorbent composite, comprising:
a plurality of wettable fibers; and,
a water swellable, water insoluble superabsorbent material in combination with the wettable fibers and having a first gel-bed friction angle at a superabsorbent material swelling level of about 2.0 grams of 0.9 weight percent sodium chloride solution/gram of the superabsorbent material and gel-bed friction angles, at superabsorbent material swelling levels greater than about 2.0 grams of 0.9 weight percent sodium chloride solution/gram of the superabsorbent material, substantially equal to or less than the first gel-bed friction angle,
wherein the first gel-bed friction angle is about 20 degrees or less.

20. The absorbent composite of claim 19, wherein the first gel-bed friction angle is about 10 degrees or less.

21. The absorbent composite of claim 19, wherein the water swellable, water insoluble superabsorbent material is selected from the group consisting essentially of natural materials, modified natural materials, synthetic materials, and combinations thereof.

22. The absorbent composite of claim 21, wherein the water swellable, water insoluble superabsorbent material is selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

23. The absorbent composite of claim 19, further comprising a friction angle reducing additive in combination with the superabsorbent material.

24. The absorbent composite of claim 23, wherein the friction angle reducing additive is selected from the group consisting essentially of glycerol, mineral oil, silicone oil, polysaccharides, polyethylene oxides, and combinations thereof.

25. The absorbent composite of claim 23, further comprising an emulsifier in combination with the superabsorbent material.

26. The absorbent composite of claim 25, wherein the emulsifier is selected from the group consisting essentially of phosphatidylcholine, lecithin, and combinations thereof.

27. The absorbent composite of claim 23, further comprising a surfactant in combination with the superabsorbent material.

28. The absorbent composite of claim 27, wherein the surfactant is selected from the group consisting essentially of sorbitan monolaurate, compounds of the Triton series, compounds of the Brij series, polyoxyethylene sorbitan monolaurate, polyoxyethylene sorbitan tetraoleate, alcohol amines, and combinations thereof.

29. The absorbent composite of claim 19, wherein the superabsorbent material further comprises a structure selected from the group consisting essentially of particles, fibers, flakes, spheres, and combinations thereof.

30. The absorbent composite of claim 19, wherein the plurality of wettable fibers is selected from the group consisting essentially of natural fibers, synthetic fibers, and combinations thereof.

31. An absorbent composite, comprising:
a plurality of wettable fibers; and,
a water swellable, water insoluble superabsorbent material in combination with the wettable fibers and having a first gel-bed friction angle at a superabsorbent material swelling level of about 2.0 grams of 0.9 weight percent sodium chloride solution/gram of the superabsorbent material and gel-bed friction angles, at superabsorbent material swelling levels greater than about 2.0 grams of 0.9 weight percent sodium chloride solution/gram of the superabsorbent material, greater than the first gel-bed friction angle, wherein the first gel-bed friction angle is about 20 degrees or less.

32. The absorbent composite of claim 31, wherein the first gel-bed friction angle is about 10 degrees or less.

33. The absorbent composite of claim 31, further comprising a friction angle increasing additive in combination with the water swellable, water insoluble superabsorbent material.

34. The absorbent composite of claim 31, further comprising a friction angle increasing additive in combination with the wettable fibers.

35. The absorbent composite of claim 33, wherein the friction angle increasing additive is selected from the group consisting essentially of chitosan, sodium silicate, sodium aluminate, alumino silicates, and combinations thereof.

36. The absorbent composite of claim 31, wherein the plurality of wettable fibers is selected from the group consisting essentially of natural fibers, synthetic fibers, and combinations thereof.

37. The absorbent composite of claim 31, wherein the water swellable, water insoluble superabsorbent material is selected from the group consisting essentially of natural materials, modified natural materials, synthetic materials, and combinations thereof.

38. The absorbent composite of claim 37, wherein the water swellable, water insoluble superabsorbent material is selected from the group consisting essentially of silica gels, agar, pectin, guar gum, alkali metal salts of polyacrylic acids, polyacrylamides, polyvinyl alcohols, ethylene maleic anhydride copolymers; polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

39. A superabsorbent material, comprising:
a water swellable, water insoluble superabsorbent material; and,
the superabsorbent material having a first gel-bed friction angle at a first superabsorbent material swelling level of the superabsorbent material and gel-bed friction angles, at superabsorbent material swelling levels greater than the first superabsorbent material swelling level of the superabsorbent material, greater than the first gel-bed friction angle,
wherein the first gel-bed friction angle is about 20 degrees or less.

40. The superabsorbent material of claim 39, wherein the first gel-bed friction angle is 10 degrees or less.

41. The superabsorbent material of claim 39, further comprising a friction angle increasing additive within the superabsorbent material in combination with the water swellable, water insoluble superabsorbent material.

42. The superabsorbent material of claim 41, wherein the friction angle increasing additive is selected from the group consisting essentially of chitosan, sodium silicate, sodium aluminate, alumino silicates, and combinations thereof.

43. The superabsorbent material of claim 39, wherein the water swellable, water insoluble superabsorbent material is selected from the group consisting essentially of natural materials, modified natural materials, synthetic materials, and combinations thereof.

44. The superabsorbent material of claim 43, wherein the water swellable, water insoluble superabsorbent material is selected from the group consisting essentially of silica gels, agar, pectin, guar gum, alkali metal salts of polyacrylic acids, polyacrylamides, polyvinyl alcohols, ethylene maleic anhydride copolymers, polyvinyl ethers, hydroxypropylcelluloses, polyvinyl morpholinones, polymers and copolymers of vinyl sulfonic acid, polyacrylates, polyacrylamides, polyvinyl pyridine, acrylonitrile grafted starch, acrylic acid grafted starch, isobutylene maleic anhydride copolymers, polyamines, and combinations thereof.

45. The superabsorbent material of claim 39, further comprising a structure selected from the group consisting essentially of particles, fibers, flakes, spheres, and combinations thereof.

46. An absorbent composite, comprising:
a plurality of wettable fibers; and,
a water swellable, water insoluble superabsorbent material in combination with the wettable fibers and having a first gel-bed friction angle at a first superabsorbent material swelling level of the superabsorbent material and gel-bed friction angles, at superabsorbent material swelling levels greater than the first superabsorbent material swelling level of the superabsorbent material, greater than the first gel-bed friction angle,
wherein the first gel-bed friction angle is about 20 degrees or less.

47. The absorbent composite of claim 46, wherein the first gel-bed friction angle is about 10 degrees or less.

48. The absorbent composite of claim 46, further comprising a friction angle increasing additive in combination with the water swellable, water insoluble superabsorbent material.

49. The absorbent composite of claim 46, further comprising a friction angle increasing additive in combination with the wettable fibers.

50. The absorbent composite of claim 48, wherein the friction angle increasing additive is selected from the group consisting essentially of chitosan, sodium silicate, sodium aluminate, alumino silicates, and combinations thereof.

51. The absorbent composite of claim 46, wherein the plurality of wettable fibers is selected from the group consisting essentially of natural fibers, synthetic fibers, and combinations thereof.

52. The absorbent composite of claim 46, wherein the water swellable, water insoluble superabsorbent material is selected from the group consisting essentially of natural materials, modified natural materials, synthetic materials, and combinations thereof.

* * * * *